(12) United States Patent
Christie et al.

(10) Patent No.: US 10,143,839 B1
(45) Date of Patent: Dec. 4, 2018

(54) LEAD NAVIGATION GUIDANCE

(71) Applicant: Medtronic, Inc., Minneapolis, MN (US)

(72) Inventors: Melissa G. T. Christie, Andover, MN (US); Ronald A. Drake, St. Louis Park, MN (US); Bushan Purushothaman, Plymouth, MN (US); Andrzej M. Malewicz, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/642,054

(22) Filed: Jul. 5, 2017

(51) Int. Cl.
| | |
|---|---|
| *A61N 1/05* | (2006.01) |
| *A61N 1/362* | (2006.01) |
| *A61N 1/08* | (2006.01) |
| *A61N 1/39* | (2006.01) |

(52) U.S. Cl.
CPC ............. *A61N 1/08* (2013.01); *A61N 1/05* (2013.01); *A61N 1/3956* (2013.01); *A61N 1/3987* (2013.01)

(58) Field of Classification Search
None
See application file for complete search history.

(56) References Cited

U.S. PATENT DOCUMENTS

| | | |
|---|---|---|
| 5,335,668 A | 8/1994 | Nardella |
| 5,536,267 A | 7/1996 | Edwards et al. |
| 5,792,204 A | 8/1998 | Snell |
| 6,546,935 B2 | 4/2003 | Hooven |
| 6,714,806 B2 | 3/2004 | Iaizzo et al. |
| 7,599,730 B2 | 10/2009 | Hunter et al. |
| 7,991,484 B1 | 8/2011 | Sengupta et al. |
| 8,180,454 B2 | 5/2012 | Greenberg et al. |
| 2003/0199938 A1 | 10/2003 | Smits et al. |
| 2004/0133113 A1 | 7/2004 | Krishnan |
| 2004/0204734 A1 | 10/2004 | Wagner et al. |
| 2006/0069419 A1 | 3/2006 | Sweeney et al. |
| 2008/0065061 A1 | 3/2008 | Viswanathan |
| 2010/0113963 A1 | 5/2010 | Smits et al. |
| 2011/0125049 A1 | 5/2011 | Nabutovsky et al. |
| 2014/0316429 A1 | 10/2014 | Smits et al. |

OTHER PUBLICATIONS

Hsia et al., "Novel Minimally Invasive, Intrapericardial Implantable Cardioverter Defibrillator Coil System: A Useful Approach to Arrhythmia Therapy in Children," Ann Thorac Surg. Apr. 2009; 87(4): 6 pgs.

(Continued)

*Primary Examiner* — Brian T Gedeon

(57) ABSTRACT

In some examples, a medical device system includes an electrode. The medical device system may include impedance measurement circuitry coupled to the electrode, the impedance measurement circuitry may be configured to generate an impedance signal indicating impedance proximate to the electrode. The medical device system may include processing circuitry that may be configured to identify a first frequency component and a second frequency component of the impedance signal, and provide an indication of a location of the electrode in a patient based on the first frequency component and the second frequency component.

40 Claims, 13 Drawing Sheets

(56) References Cited

OTHER PUBLICATIONS

Burkland, et al., "Near-Field Impedance Accurately Distinguishes Among Pericardial, Intracavitary, and Anterior Mediastinal Position", J. Cardiovasc. Electrophysiol., 2017, vol. 28, 8 pages.

Trebbels et al., "Real-Time Cannula Navigation in Biological Tissue with High Temporal and Spatial Resolution Based on Impedance Spectroscopy", 32 Annual International Conference of the IEEE EMBS, Buenos Aires, Argentina, Aug. 31-Sep. 4, 2010, 4 pages.

(PCT/US2018/040731) PCT Notification of Transmittal of the International Search Report and the Written Opinion of the International Searching Authority, dated Sep. 18, 2018, 14 pages.

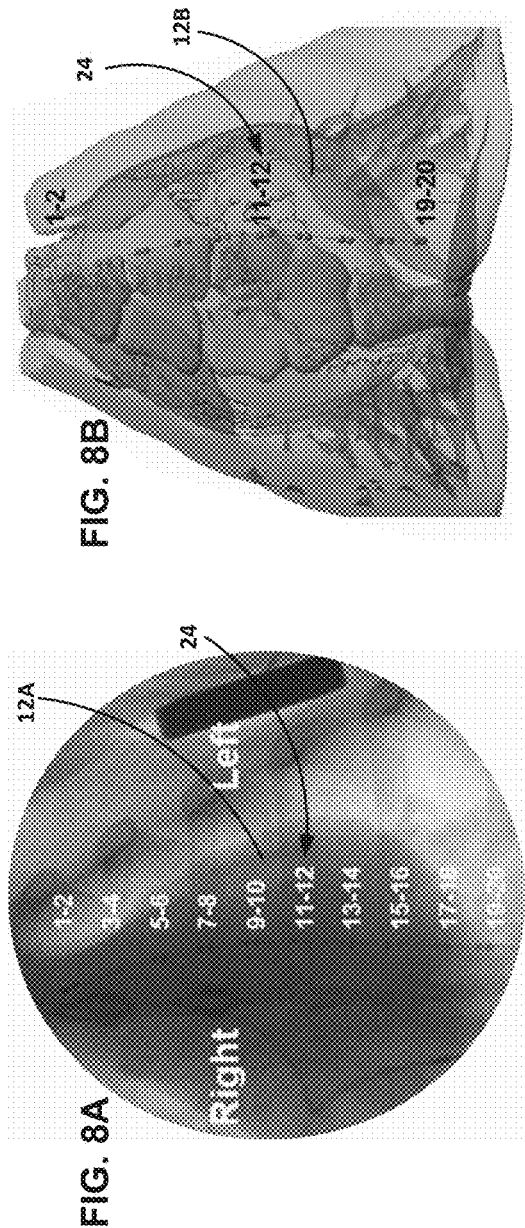
FIG. 8A
FIG. 8B
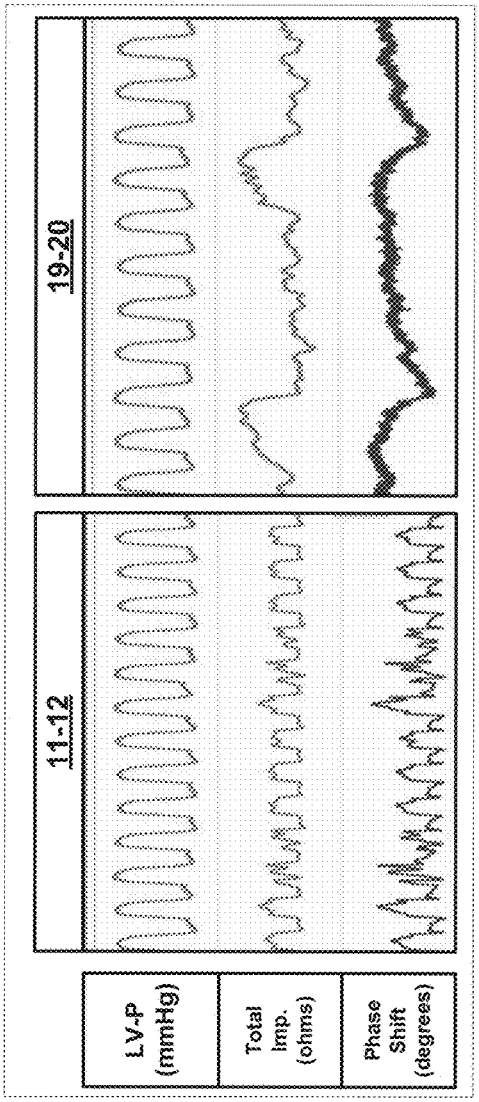
FIG. 8C

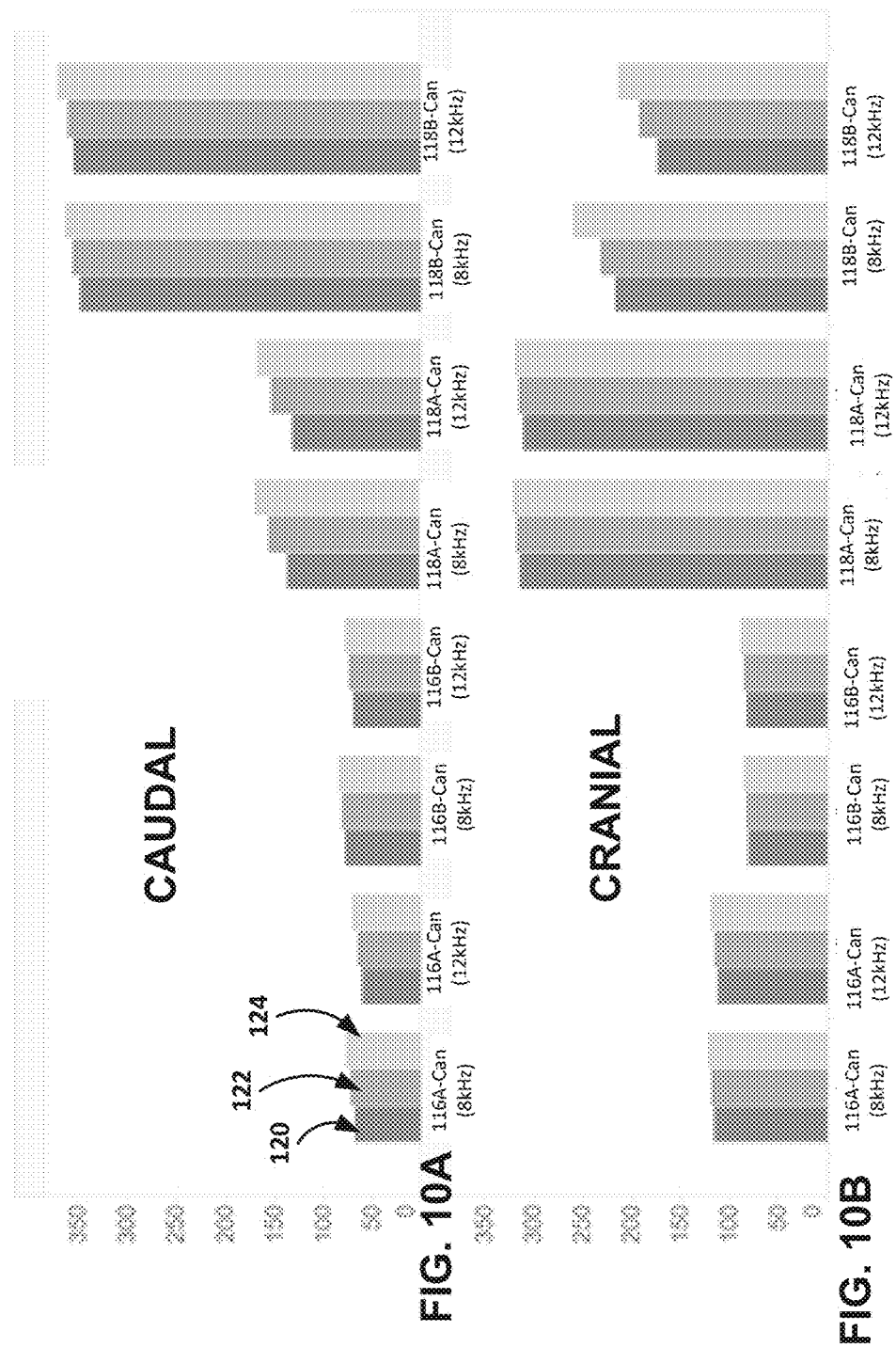

LEAD NAVIGATION GUIDANCE

TECHNICAL FIELD

This disclosure relates to medical devices, and more particularly, to techniques for implanting medical devices, such as implantable medical electrical leads.

BACKGROUND

Implantable pulse generators have been used to provide electrical stimulation to organs, tissues, muscles, nerves, or other parts of a patient's body. One example of electrical stimulation is cardiac pacing. Cardiac pacing includes electrically stimulating the heart when heart's natural pacemaker or conduction system fails to provide synchronized atrial and ventricular contractions at appropriate rates and intervals for the patient's needs. When the patient's heart is beating too slowly, bradycardia pacing increases the rate at which the patient's heart contracts to provide relief from symptoms associated with bradycardia. Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes. Cardiac pacing may also provide electrical stimulation intended to suppress or convert tachyarrhythmias. This may supply relief from symptoms, and prevent or terminate arrhythmias that could lead to sudden cardiac death or the need to be treated with high voltage defibrillation or cardioversion shocks.

Traditional implantable pulse generators include a housing that encloses a pulse generator and other electronics, and is implanted subcutaneously in the chest of the patient. The housing is connected to one or more implantable medical electrical leads. The electrical lead includes one or more electrodes on a distal portion of the lead that is implanted inside the patient, such as inside the patient's heart (e.g., such that at least one of the electrodes contacts the endocardium), within vasculature near the heart (e.g., within the coronary sinus), or attached to the outside surface of the heart (e.g., in the pericardium or epicardium).

SUMMARY

This disclosure, among other things, describes systems and techniques for implantation of an implantable medical electrical lead. One aspect of this disclosure includes methods for guiding navigation during implantation of the lead within extracardiovascular locations within a patient. The extracardiovsasular locations may include subcutaneous and/or substernal locations. Subcutaneous leads do not intimately contact the heart, but instead reside in a plane of tissue or muscle between the skin and sternum. Likewise, substernal leads do not intimately contact the heart, but instead reside in a plane of tissue or muscle between the sternum and the heart.

Due to the distance between the heart and electrodes of one or more leads implanted in the patient, to achieve improved pacing, sensing, or defibrillation, the pace/sense electrodes and the defibrillation coil electrode should be positioned in the plane of tissue such that the electrodes are located directly above or proximate the surface of the cardiac silhouette. For example, the one or more electrodes used to deliver pacing pulses should be positioned in a vector over substantially the center of the chamber to be paced to produce the lowest pacing capture thresholds for pacing. Likewise, the one or more electrodes used to sense cardiac electrical activity of the heart should be positioned over substantially the center the chamber to be sensed to obtain the best sensed signal. For shocking purposes, it is preferred to have the defibrillation coil electrode positioned over substantially the center the chamber to be shocked.

Navigating the lead to such desired positions described herein may be improved by providing navigation guidance to a user, such as a physician, during the implantation procedure. The systems and techniques described herein include determining a location of the lead relative to one or more organs or other anatomical structures of a patient. For example, a relative location of an electrode on the lead within a patient may be indicative of the lead's position relative to the patient's heart or lungs. The medical device system may provide an indication of the relative location of an electrode (e.g., placed on a substernally implantable electrical stimulation lead) relative to a patient's heart and lungs based on an impedance signal indicating impedance proximate to the electrode. By using the systems and techniques described herein, a lead may be placed with more precision, reliability, and repeatability (e.g., from patient to patient). A navigation system may improve functionality of the lead, such as by providing more or better information about the substernal space during navigation and placement of the lead in the patient. By using impedance information about the substernal space (e.g., including from a carrier signal between two electrodes), navigating and placing a substernally implantable electrical stimulation lead may be performed safer and more efficiently. Further, the systems and techniques described herein may be utilized in other anatomical spaces, such as within the heart or proximate to other organs. For example, the medical device system described herein may be used with left ventricular lead implants such as to provide impedance mapping functionality, with an electrocardiogram (ECG) belt to provide more information during a medical diagnosis or therapy, or with another mapping system (e.g., a CardioInsight™ Noninvasive 3D Mapping System, available from Medtronic plc, of Dublin, Ireland).

In an example, this disclosure is directed to a method for indicating a relative location of an electrode in a patient, the method comprising generating, by impedance measurement circuitry coupled to the electrode, an impedance signal indicating impedance proximate to the electrode; identifying, by processing circuitry, a first frequency component and a second frequency component of the impedance signal; and providing, by the processing circuitry and to a user, an indication of the relative location of the electrode in the patient based on the first frequency component and the second frequency component.

In an example, this disclosure is directed to a medical device system comprising: an electrode; impedance measurement circuitry coupled to the electrode, the impedance measurement circuitry configured to generate an impedance signal indicating impedance proximate to the electrode; and processing circuitry configured to identify a first frequency component and a second frequency component of the impedance signal; and provide an indication of a relative location of the electrode in a patient based on the first frequency component and the second frequency component.

In an example, this disclosure is directed to a medical device system comprising: an electrode; impedance measurement circuitry coupled to the electrode, the impedance measurement circuitry configured to generate an impedance signal indicating impedance proximate to the electrode; and processing circuitry configured to: identify a first frequency component of the impedance signal corresponding to a cardiac contraction frequency and a second frequency component of the impedance signal corresponding to a respiration frequency; determine a first amplitude of the first frequency component and a second amplitude of the second frequency component; determine a relationship between the first amplitude and the second amplitude; and provide an indication of a relative location of the electrode in a patient based on the relationship.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF DRAWINGS

FIGS. 8A and 8B illustrate examples of substernal space locations in a patient.

FIG. 8C illustrates graphs of examples including impedance signals for different locations in a substernal space of a patient.

FIG. 10A-10E illustrate examples of techniques for determining a relative location of an electrode in a patient.

Figure 1A:
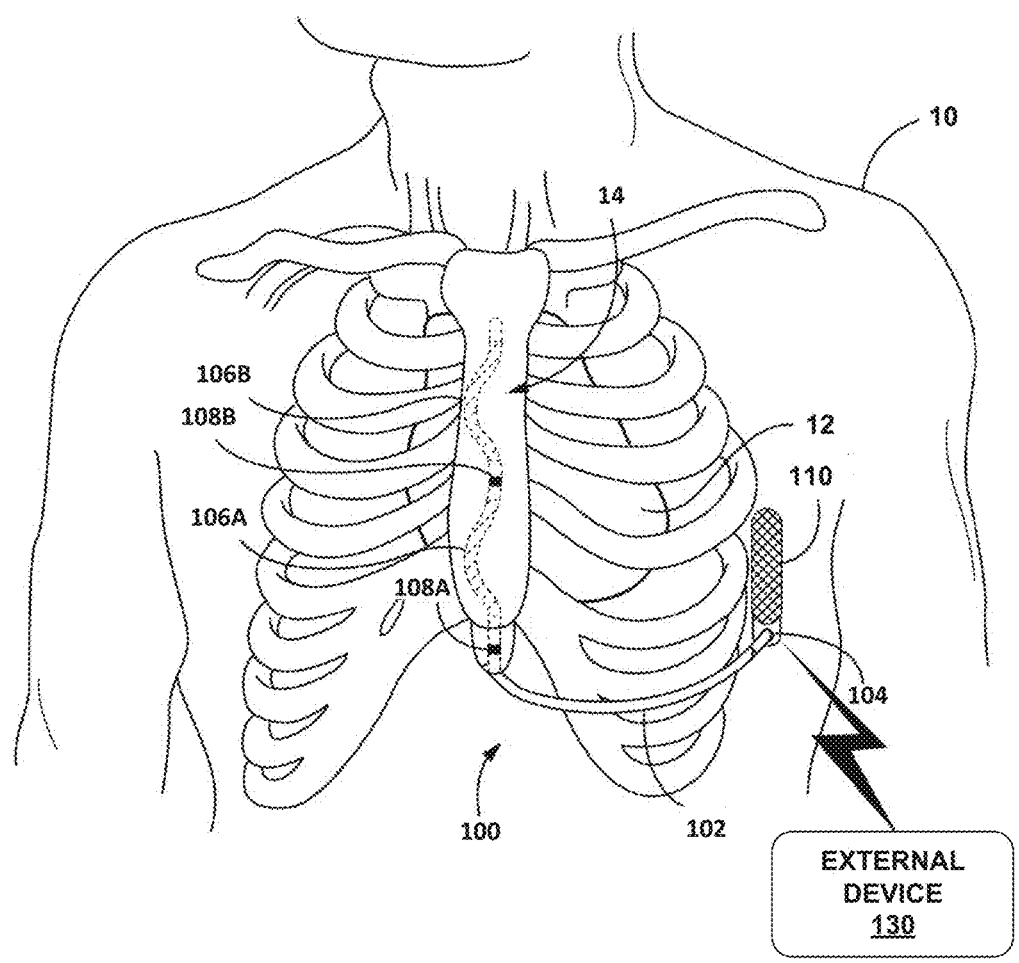
FIGS. 1A-1C are front-view, side-view, and top-view conceptual drawings, respectively, illustrating an example medical device system in conjunction with a patient.

The details of one or more examples of this disclosure are set forth in the accompanying drawings and the description below. Other features, objects, and advantages of this disclosure will be apparent from the description and drawings, and from the claims.

DETAILED DESCRIPTION

In this disclosure, techniques, systems, devices, components, assemblies, and methods for guiding the navigation of a lead into a targeted delivery site, e.g., within a substernal space, are described. For delivery to the substernal space, the lead may be delivered through a surgical incision created on the skin or tissue adjacent to or below the xiphoid process (also referred to as "subxiphoid") to form an access point to the substernal space, and advancing the lead with the aid of a navigation system to a desired position within the substernal space. The access point may also be formed at the notch that connects the xiphoid process to the sternum. In other examples, the substernal space may also be accessed through the manubrium. By using the systems and techniques described herein, a lead may be safely navigated into the substernal space, or other target locations, and more optimal lead placement may be achieved.

In general, a medical device system may include one or more electrodes, such as placed on the lead or such as a housing electrode. Impedance measurement circuitry may use two or more electrodes to generate an impedance signal therebetween. In some examples, the impedance signal is indicative of the impedance proximate to one of these electrodes. In an example of a lead having four electrodes, an impedance signal may be generated for each electrode, where the respective four vectors are between each of the four electrodes and a can electrode. In an example, the impedance signal may be indicative of the impedance proximate to the electrode on the lead, including when the electrode on the lead is a cathode or when the electrode on the lead is an anode.

In an example, an impedance signal may be generated between any two electrodes, such as two electrodes on the same lead. As such, the impedance signal may be indicative of the impedance proximate to, for example, the cathode. In an example, the electrodes used for impedance measurements may be monopolar, although being monopolar may not be required. For example, a monopolar configuration where an electrode is on the lead or a delivery tool may be used, and the position of the electrode may change as the lead or delivery tool is being implanted. In an example, electrodes of different sizes may be used (e.g., the can or a patch). In an example, the tissue proximate the smaller of the electrodes that form the vector may drive the impedance signal.

In some examples, a high frequency carrier signal may be injected between electrodes, e.g., a coil electrode and a housing electrode, and the resulting impedance signal may be indicative of the impedance proximate to the lead electrode. The high frequency signals may include frequencies of about 0.1 Hz to about 1 MHz, such as about 4 Hz to about 100 kHz. In other examples, other types of signals may be injected via the same electrodes or other electrodes to facilitate the impedance measurement.

As the location of the electrode on the lead changes while the lead is being implanted into the patient, the impedance signal may change. By using the systems and techniques described herein, a relative location of a lead may be determined without fluoroscopic imaging information. In some examples, the systems and techniques described herein may be compatible with fluoroscopic imaging, but may not require such imaging to position the lead safely in a suitable location in the substernal space.

The impedance signal may comprise one or more frequency components. For example, a first frequency component of the impedance signal corresponds to a cardiac contraction frequency, and a second frequency component of the impedance signal corresponds to a respiration frequency. The processing circuitry may identify such frequency components, or other components of the impedance signal. The processing circuitry provides to a user an indication of the relative location of the electrode based on the first and second frequency components. For example, as the lead is being implanted, the techniques described herein make it possible to indicate the relative distance to the heart and the lungs, or a relative location of the lead in the patient, such as based on the first and second frequency components. In this way, an appropriate position of the lead, based on the electrode configuration on the lead and the patient's anatomy, may be achieved. In an example, the systems and techniques described herein include detecting a change in the location of the lead, such as detecting lead migration after the implantation procedure is complete. In some examples, the processing circuitry provides to a user an indication of the relative location of the electrode based on other components of the impedance signal, such as higher level frequency components (e.g., harmonics of the first or second frequency components).

In other examples, the processing circuitry may determine a state of the patient or a state of an organ of the patient, such as a change in fluid content in tissues within the patient's thoracic cavity, a change in the heart's contribution to an impedance signal, or a change in a lung's contribution to an impedance signal, such as may be due to a shift in the location of the lead within the substernal space after the implantation procedure or a change in posture of the patient. In some examples, the processing circuitry may determine the presence of air pockets or assess air pockets around the electrodes. The impedance signal may be modulated by saline injected into the patient or by vacuum use during the implant procedure. In some examples, using a vacuum during the procedure may minimize the chance of the introduction of air into the implant space.

The processing circuitry may determine a characteristic of the first frequency component. The characteristic of the first frequency component may be referred to as the first characteristic. Likewise, the processing circuitry may determine a characteristic of the second frequency component, and characteristic of the second frequency component may be referred to as the second characteristic. The first and second characteristics, which may individually or collectively be referred to as "the characteristic," may correspond to an amplitude, frequency, wavelength, a power or intensity in Fourier space, another signal characteristic, or any combination thereof. In some examples, the characteristic is based on or determined by a function. In some examples, the characteristic is based on or determined by a hardware filter, a software filter, or a combination of the two. The processing circuitry may provide the indication of the relative location of the electrode in the patient based on the first characteristic and the second characteristic.

The processing circuitry may determine a relationship between the first characteristic and the second characteristic. In an example, the relationship is a ratio. In another example, the relationship is a function, and may include a weighting factor. The first characteristic may correspond to an amplitude of a cardiac contraction frequency component (e.g., first frequency component) of an impedance signal. The second characteristic may correspond to an amplitude of a respiration frequency component (e.g., second frequency component) of the impedance signal. In this example, the relationship is a ratio of the second characteristic to the first characteristic (e.g., ratio of respiration impedance to heart impedance). In an example, the relationship may be a ratio of the first characteristic to the second characteristic. By using the relationship between the first and second characteristics, the system may provide the relative location of the electrode. In this way, when the ratio is relatively larger, then that may be an indication that the corresponding electrode is closer to the patient's lung than the patient's heart. When the ratio is relatively smaller, then that may be an indication that the corresponding electrode is closer to the patient's heart than the patient's lung. As such, a defibrillation electrode, for example, may be safely navigated to an appropriate location in the substernal space.

In an example, when the ratio is relatively larger, the ratio may be larger than a previously measured ratio (e.g., a temporal relativity). In this way, the navigation system may indicate that the lead (e.g., the electrode on the lead) is getting closer to the patient's lung over time, and this may indicate that the lead is getting further from the patient's heart over time.

In an example, a relatively larger ratio may refer to a ratio that is greater than a threshold value (e.g., 0.9, 1.0, 1.1, or another value). For example, when the second characteristic corresponding to the amplitude of the respiration frequency component is greater than the first characteristic corresponding to the amplitude of the cardiac contraction frequency component, then the ratio may be greater than 1. As such, this may be an indication that the electrode is relatively closer to the lung than the heart. In a similar way, a relatively smaller ratio that is less than a threshold value (e.g., 1.0, 0.6, 0.4, or another value) may indicate that the electrode is relatively closer to the heart than the lung.

In an example, a relatively larger ratio may refer to a relationship between multiple ratios (e.g., multiple ratios as corresponding to a respective multiple electrodes). Therefore, a relatively larger ratio may be larger than another ratio (e.g., as in electrode 118B relative to the other electrodes in FIG. 10D).

In general, the processing circuitry may use more than one ratio value (e.g., a ratio over time, a ratio threshold value, multiple ratios for multiple electrodes) for providing the indication of the relative location. The relative location may refer to a location of the electrode relative to one or more organs, tissues, bones, or the like. For example, the relative location of the electrode may include or refer to being relative to at least one of the patient's sternum, heart, lung, or portion of the patient's heart or lung. In an example, the relative location may additionally or alternatively include or refer to at least one of a relative cranial-caudal location of the electrode, a relative left-right lateral location of the electrode, or a relative ventral-dorsal location of the electrode. One or more indications may be provided over time, such as periodically or continuously, as the relative location changes (e.g., such as during an implantation procedure). Information about the relative location, as described herein, of the lead or electrode may supplement information from other sources, such as an imaging system. In some examples, the indication of the relative location of an electrode or of the lead comprises information on a map, such as to provide impedance mapping to aide in navigation and lead placement. In an example, the indication may comprise an alert, such as may include a sound, a light, or pop-up window on a display to the user. The indication may comprise one or more types of indications, and may comprise information from other sources, such as medical imaging information or a pre-loaded patient anatomy map. In an example, such impedance mapping may be implemented using different combinations of electrodes, such as a signal between defibrillation electrodes, pace or sense electrodes, a housing or housing electrode, or any combination thereof. In some examples, the indication includes a relative distance of an electrode or lead to the heart and lungs of the patient.

In some examples, by using the relationship between the first and second characteristics, the system may provide an indication that the electrode is suitably positioned. For example, the techniques and navigation system described herein may determine satisfactory positioning within the substernal space. In some examples, this may not require determining the relative location of the electrode. For example, the processing circuitry may determine that the relationship between the first and second characteristics satisfies a criterion or set of criteria, e.g., a threshold value or threshold range of values. In an example, a satisfactory ratio (e.g., using values described herein) of respiration to cardiac amplitude may be used. In an example, the techniques and systems described herein may determine an electrode vector based on the relationships (e.g., ratios) described herein.

In some examples, the impedance signal may be used to determine absolute impedance. Absolute impedance, such as may be combined with the ratio, may be used to determine a location of the lead (e.g., a relative location, in a air pocket of the implant space, a determination of inside or outside the pericardial sac, or other location information).

Other information may be determined from the impedance signal. For example, the impedance signal morphology may contain information about relative distances between components of the medical device system and an organ, or other information about organs, such as respiration rate, heart rate, thoracic impedance, or a state of edema in the patient. This information may be used to determine the relative location of the lead in the patient, or to inform suitable patient therapy parameters. In some examples, such information may be used for ongoing therapy or ongoing monitoring (e.g., ongoing respiratory monitoring). In some examples, the processing circuitry may use such information to monitor the lead after implantation, such as to determine a change in the position of the implanted lead. In some examples, the processing circuitry may use such information to determine a change in body structures of the patient, a change in lead properties, e.g., lead integrity, or a change in the electrode-tissue interface.

In an example, the information determined from the impedance signal (e.g., relative location of an electrode, suitable position, signal characteristics, or other information) may be used to determine the electrode vector for therapy or sensing. The information, for example, may be used to determine multiple vectors available from multiple electrodes. The processing circuitry described herein may determine such vectors.

The lead may be implanted with the aid of a delivery system. The delivery system may include an implant tool. For example, the implant tool comprises an elongate tool, a sheath, and a handle. In some examples, the implant tool comprises one or more electrodes, such as on the elongate tool, the sheath, or both. By using the systems and techniques described herein with the delivery system, the lead may be placed such that a therapy vector between a defibrillation electrode on the lead and a housing or can electrode is substantially across the ventricle of the heart. In some examples, the lead may be implanted substantially centered under the patient's sternum. In other examples, the lead may be implanted such that it is offset laterally from the center of the sternum. The implant tool may define a channel configured to receive a medical lead, for implanting the medical lead into the substernal space.

Figure 5A:
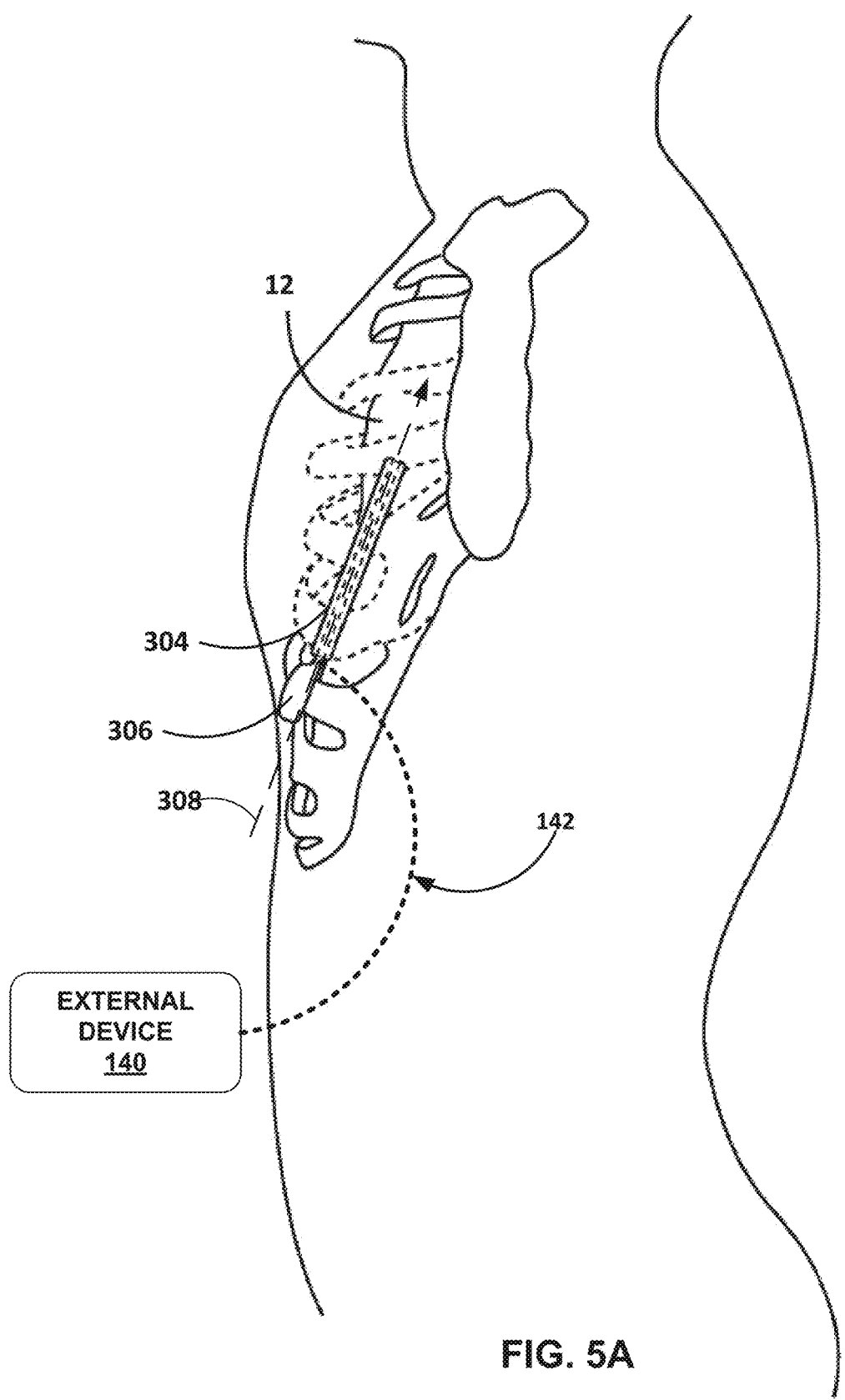
FIG. 5A is a partial perspective view that illustrates a portion of a technique of implanting a lead.
Figure 5B:
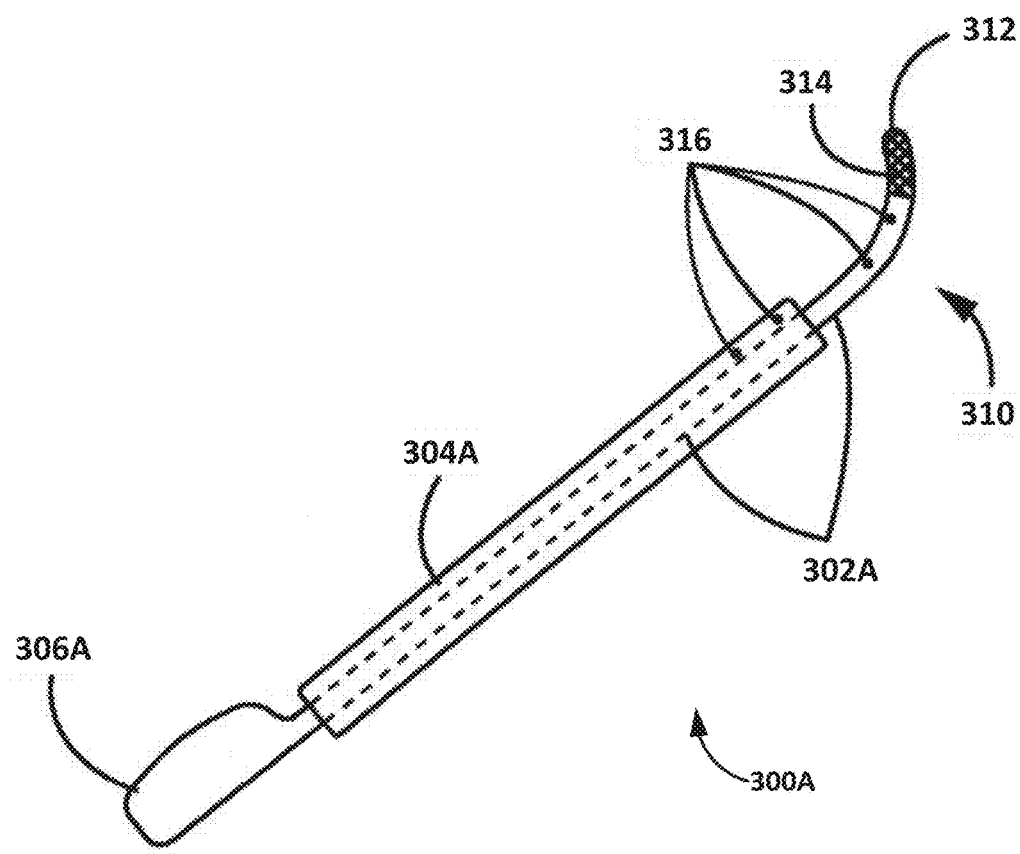
FIG. 5B is a perspective view that illustrates a portion of a lead delivery system.

In some examples, the delivery system may include one or more electrodes, such as on a distal section of the elongate tool or a distal section of the sheath, such as described with respect to FIG. 5B. The one or more electrodes on the implant tool may be positioned at other locations, such as a proximal section of the sheath. An impedance signal may be generated using the one or more electrodes on the implant tool. The impedance signal generated using the one or more electrodes on the implant tool may be used in the same or a similar way as the impedance signal for the one or more electrodes on the medical lead. By using the techniques described herein, the implant tool may be guided to an appropriate location in the patient, such to allow for more efficient implantation of the lead.

In some examples, the lead or tool includes a plurality of electrodes. As such, the impedance measurement circuitry may generate a plurality of impedance signals, each signal indicating impedance proximate to a respective one of the plurality of electrodes. First and second frequency components may be identified by processing circuitry for each of the plurality of impedance signals. Providing the indication of the relative location of the lead in the patient may be based on the first and second frequency components of the plurality of impedance signals.

In some examples, the processing circuity provides an indication of the relative location of one or more of the plurality of electrodes. In some examples, the indication of the relative location of one of the plurality of electrodes is based on the relative location of at least one other electrode of the plurality of electrodes. That is, for each of the plurality of electrodes, a ratio between the first and second characteristics may be compared to another ratio of one or more of the other electrodes of the plurality of electrodes. The indication of the relative location of an electrode may be based on a result of the comparison.

Figure 1B:
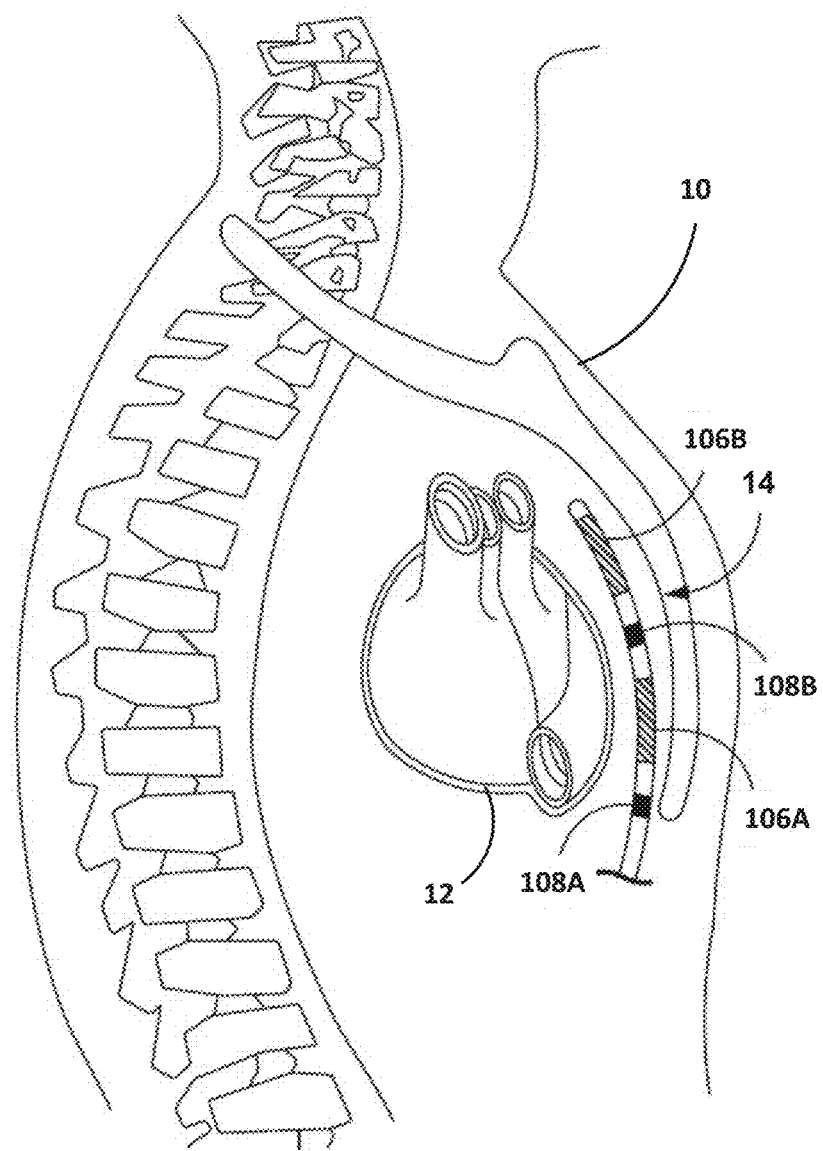
Figure 1C:
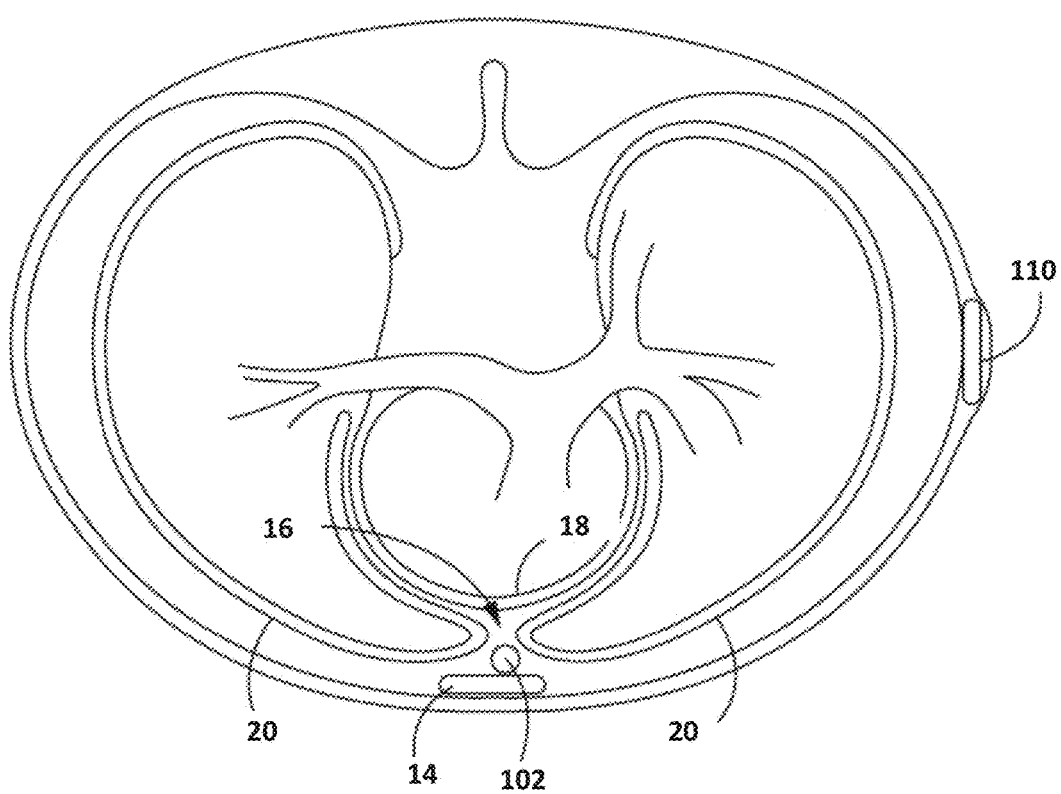

FIGS. 1A-1C are front-view, side-view, and top-view conceptual drawings, respectively, illustrating an example of a medical device system 100 (also referred to as "system 100") in conjunction with a patient 10. The systems and techniques described herein may be used for lead navigation and positioning. For example, by providing one or more indications about a relative location of an electrode on a lead of the medical device system, healthcare providers may implant the lead more safely and efficiently.

In the illustrated example, the medical device system 100 is an extracardiovascular implantable cardioverter defibrillator (ICD) system implanted within patient 10. However, these techniques may be applicable to other cardiac systems, including cardiac pacemaker systems, cardiac resynchronization therapy defibrillator (CRT-D) systems, cardioverter systems, or combinations thereof, as well as other stimulation and/or sensing systems, such as neurostimulation systems. Further, although described primarily in the context of implanting leads, the techniques may be applicable to implantation of other devices, such as leadless implantable stimulators including electrodes on their housings. In addition, system 100 may not be limited to treatment of a human patient. In alternative examples, system 100 may be implemented in non-human patients, such as primates, canines, equines, pigs, bovines, ovines, and felines. These other animals may undergo clinical or research therapies that may benefit from the subject matter of this disclosure.

In general, systems (e.g., system 100) may include one or more medical devices, leads, external devices, or other components configured for techniques described herein. In the illustrated example, ICD system 100 includes an implantable medical device (IMD) 110, which is an ICD and is referred to hereafter as ICD 110. ICD 110 is connected to at least one implantable cardiac defibrillation lead 102. In some examples, two leads are used. ICD 110 may be configured to deliver high-energy cardioversion or defibrillation pulses to a patient's heart 12 when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 110.

ICD 110 may also be configured to provide a signal, e.g., a high frequency carrier signal, between two electrodes of ICD 110. By providing a signal between two electrodes and determining an impedance signal, a lead location relative to heart 12 or lungs of patient 10 may be indicated, such as to a healthcare provider during implantation of lead 102, as described further below.

In an example, ICD 110 may comprise all or part of a navigation system. The navigation system may be used for guiding the navigation and placement of lead 102 into the substernal space. In some examples, an external device, e.g., external device 130, may comprise all or part of the navigation system (e.g., such as described further below). For example, ICD 110 may comprise one or more electrodes coupled (e.g., communicatively coupled) to impedance measurement circuitry of a navigation system, and an external device may comprise processing circuitry configured to identify a first frequency component and a second frequency component of an impedance signal sensed by the one or more electrodes and received from the ICD by the external device. Or, ICD 110 may fully comprise the navigation system, and may provide an indication of the relative location of the lead, e.g., to external device 130, using processing circuitry.

ICD 110 is implanted subcutaneously or submuscularly on the left side of patient 10 above the ribcage. Defibrillation lead 102 may be implanted at least partially in a substernal space, e.g., between the ribcage or sternum 14 and heart 12. In one such configuration, a proximal portion of lead 102 extends subcutaneously from ICD 110 toward sternum 14 and a distal portion of lead 102 extends superior under or below sternum 14 in the anterior mediastinum 16 (FIG. 1C). The anterior mediastinum 16 is bounded laterally by the pleurae 20 (FIG. 1C), posteriorly by the pericardium 18 (FIG. 1C), and anteriorly by the sternum 14. In some instances, the anterior wall of the anterior mediastinum may also be formed by the transversus thoracics and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102 extends along the posterior side of the sternum 14 substantially within the loose connective tissue or substernal musculature of the anterior mediastinum.

In general, "substernal space" may refer to the region defined by the undersurface between sternum 14 and the body cavity but not including pericardium 18. In other words, the region is posterior to the sternum 14 and anterior to the ascending aorta. The substernal space may alternatively be referred to by the terms "retrosternal space" or "mediastinum" or "infrasternal" as is known to those skilled in the art and includes the region referred to as the anterior mediastinum. For ease of description, the term substernal space will be used in this disclosure, it being understood that the term is interchangeable with any of the other aforementioned terms. Further, although described primarily in the context of delivery of a lead to the substernal space, the systems and techniques described herein may be used for lead or device guidance in the subcutaneous space, such as for safer implant procedures under the skin, or to any other location within the patient, in other examples.

In this disclosure, the term "extra-pericardial" space may refer to a region around the outer heart surface, but not within the pericardial sac or space. The region defined as the extra-pericardial space includes the gap, tissue, bone, or other anatomical features around the perimeter of, and adjacent to the pericardium.

Lead 102 may be at least partially implanted in other intrathoracic locations, such as other non-vascular, extra-pericardial locations, including the gap, tissue, or other anatomical features around the perimeter of and adjacent to, but not attached to, the pericardium or other portion of the heart and not above the sternum 14 or ribcage. In an example, the systems and techniques described herein include providing the indication of the lead during navigation through the substernal space for implantation where the electrode is being positioned within the pericardial space. For example, the distal portion of the lead with the electrode may be guided to be between the pericardium and the heart. The processing circuitry may provide an indication to the user that the lead is about to or has entered the pericardial space, such as based on a change in impedance. In an example, the impedance signal may change when the electrodes on the lead encounter (e.g., contact, couple to, or are surrounded by) liquid. Therefore, for example, the impedance signal indicated by the lead entering the pericardial space may provide a unique impedance morphology.

In other examples, lead 102 may be implanted at other extracardiovascular locations. For example, defibrillation lead 102 may extend subcutaneously above the ribcage from ICD 110 toward a center of the torso of patient 10, bend or turn near the center of the torso, and extend subcutaneously superior above the ribcage or sternum 14. Defibrillation lead 102 may be offset laterally to the left or the right of the sternum 14 or located over the sternum 14. Defibrillation lead 102 may extend substantially parallel to the sternum 14 or be angled lateral from the sternum 14 at either the proximal or distal end.

Defibrillation lead 102 includes an insulative lead body having a proximal end that includes a connector 104 configured to be connected to ICD 110 and a distal portion that includes one or more electrodes. Defibrillation lead 102 also includes one or more conductors that form an electrically conductive path within the lead body and interconnect the electrical connector and respective ones of the electrodes.

Defibrillation lead 102 includes a defibrillation electrode that includes two sections or segments 106A and 106B (individually or collectively "defibrillation electrode(s) 106"). In other examples, lead 102 includes more than one defibrillation electrode, such that electrode 106A may be a separate electrode from electrode 106B. The defibrillation electrode 106 is toward the distal portion of defibrillation lead 102, e.g., toward the portion of defibrillation lead 102 extending along the sternum 14. Defibrillation lead 102 is placed below or along sternum 14 such that a therapy vector between defibrillation electrodes 106A or 106B and a housing electrode formed by or on ICD 110 (or other second electrode of the therapy vector) is substantially across a ventricle of heart 12. The therapy vector may, in one example, be viewed as a line that extends from a point on defibrillation electrode 106 (e.g., a center of one of the defibrillation electrode sections 106A or 106B) to a point on the housing electrode of ICD 110. Defibrillation electrode 106 may, in one example, be an elongated coil electrode.

Defibrillation lead 102 may also include one or more sensing electrodes, such as sensing electrodes 108A and 108B (individually or collectively, "sensing electrode(s) 108"), located along the distal portion of defibrillation lead 102. In the example illustrated in FIG. 1A and FIG. 1B, sensing electrodes 108A and 108B are separated from one another by defibrillation electrode 106A. In other examples, however, sensing electrodes 108A and 108B may be both distal of defibrillation electrode 106 or both proximal of defibrillation electrode 106. In other examples, lead 102 may include more or fewer electrodes at various locations proximal or distal to defibrillation electrode 106. In the same or different examples, ICD 110 may include one or more electrodes on another lead (not shown).

Although referred to herein as "defibrillation electrodes" and "sensing electrodes," electrodes 106, 108 may correspond to, for example, a device other than ICD 110. In some examples, "defibrillation electrodes" as used herein may include coil electrodes, that may pace or sense in some instances. In some examples, "sensing electrodes" as used herein may include ring, tip, segmented, or semispherical electrodes, that may pace in some instances.

Lead 102 may be configured in different sizes and shapes, such as may appropriate for purposes (e.g., different patients or different therapies). In some examples, the distal portion of lead 102 may have one or more curved sections, such as shown in FIG. 1A. In some examples, the distal portion of lead 102 may be straight (e.g., straight or nearly straight). Other lead configurations may be used, such as various electrode arrangements. For example, a sensing electrode may be placed between two defibrillation electrodes, such as described above. In an example, multiple sensing electrodes may be placed between two defibrillation electrodes. In an example, two defibrillation electrodes may not be separated by a sensing electrode. Other arrangements may additionally or alternatively be used.

In an example, the electrode arrangement on lead 102 may correspond to a geometry of lead 102. For example, sensing electrodes may be positioned on relative peaks of a curved lead shape, while defibrillation electrodes may be positioned on relative valleys of the curved lead shape. In other examples, the distal portion of lead 102 may include branches, biased portions expanding away from a central shaft, or other shapes (e.g., with one or more electrodes disposed on the branches, shaft, or biased portions) that may provide appropriate monitoring information or therapy.

The systems and techniques described herein may be implemented using different types of leads (e.g., as described above or other lead shapes, lead configurations, and the like), including leads designed for different types of therapies (e.g., cardiac defibrillation, cardiac pacing, spinal cord stimulation, or brain stimulation). The systems and techniques described herein may be implemented using, for example, delivery systems (e.g., a sheath or an elongate tool) or other devices that may be inserted into a patient (e.g., the substernal space of the patient).

In general, for example, ICD system 100 may sense electrical signals, such as via one or more sensing vectors that include combinations of electrodes 108A and 108B and the housing electrode of ICD 110. In some examples, ICD 110 may sense cardiac electrical signals using a sensing vector that includes one of the defibrillation electrode sections 106A and 106B and one of sensing electrodes 108A and 108B or a housing electrode of ICD 110. The sensed electrical intrinsic signals may include electrical signals generated by cardiac muscle and indicative of depolarizations and repolarizations of heart 12 at various times during the cardiac cycle. ICD 110 analyzes the electrical signals sensed by the one or more sensing vectors to detect tachyarrhythmia, such as ventricular tachycardia or ventricular fibrillation. In response to detecting the tachyarrhythmia, ICD 110 may begin to charge a storage element, such as a bank of one or more capacitors, and, when charged, deliver one or more defibrillation pulses via defibrillation electrode 106 of defibrillation lead 102 if the tachyarrhythmia is still present. Additionally or alternatively, ICD 110 may deliver pacing therapy, such as via electrodes 106, 108 and or the housing electrode of ICD 110. In an example, the pacing therapy includes antitachycardia pacing (ATP). To position lead 102 at such locations, delivery system 300 may be used with navigation system 200 such as described further below.

In some examples, external device 130 may be a computing device, e.g., used in a home, ambulatory, clinic, or hospital setting, to communicate with ICD 110 via wireless telemetry. Examples of communication techniques used by ICD 110 and external device 130 include radiofrequency (RF) telemetry, which may be an RF link established via Bluetooth, WiFi, or medical implant communication service (MICS). The communication may include one-way communication in which one device is configured to transmit communication messages and the other device is configured to receive those messages. The communication may instead include two-way communication in which each device is configured to transmit and receive communication messages.

External device 130 may be configured to comprise all or part the navigation system as described herein. In one example, external device 130 comprises communication circuitry configured to communicate per the techniques described above. External device 130 may be used to program commands or operating parameters into ICD 110 for controlling its functioning, such as when configured as a programmer for ICD 110. External device 130 may be used to communicate with ICD 110, such as to retrieve data, including device operational data as well as physiological data accumulated in IMD memory, such as information about the location of lead 102 relative to one or more organs, such as based on impedance information sensed by electrodes 106, 108 or the housing electrode. External device 130 may be, as examples, a navigation guidance system, a programmer, external monitor, or consumer device, such as a smartphone. External device 130 may be coupled to a remote patient monitoring system, such as Carelink®, available from Medtronic plc, of Dublin, Ireland.

A user may program or update therapy parameters that define therapy, or perform any other activities with respect to ICD 110. The user may be a physician, technician, surgeon, electrophysiologist, or other healthcare professional. In an example, the user may be patient 10.

Figure 2:
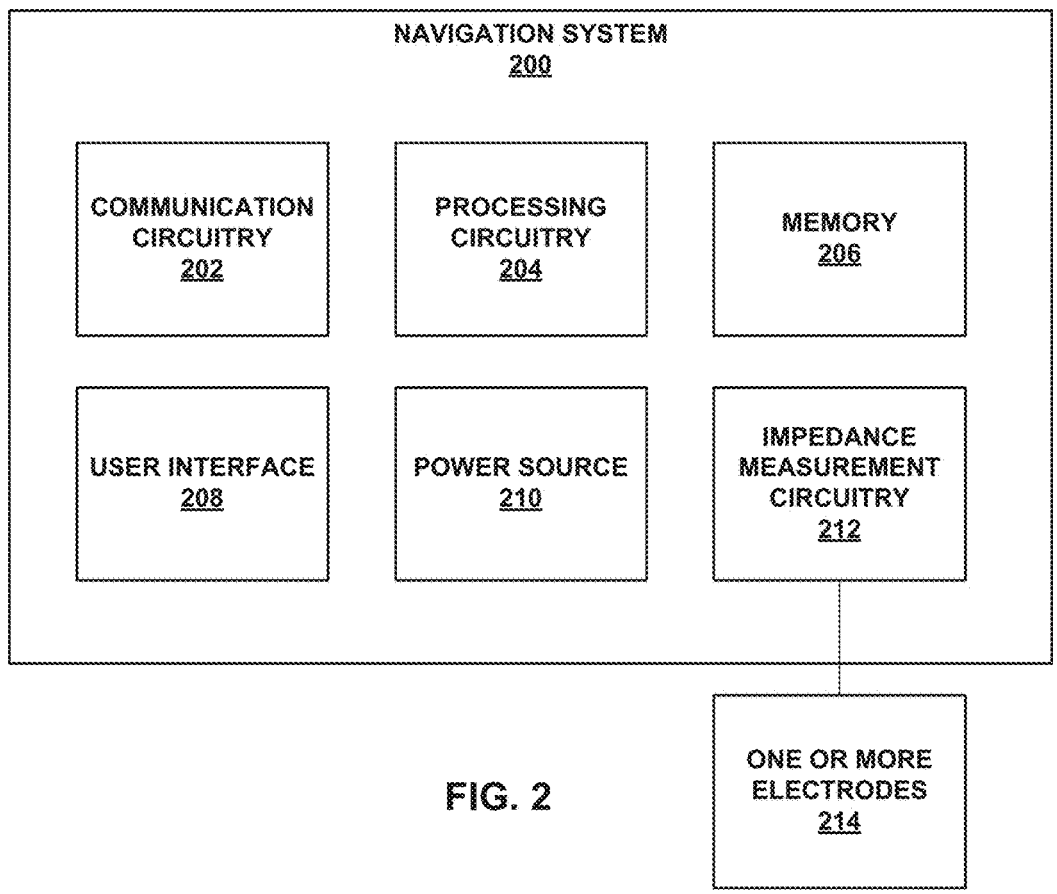
FIG. 2 is a functional block diagram illustrating an example of a navigation system.

FIG. 2 is a functional block diagram illustrating an example of a navigation system 200. In some examples, ICD 110 comprises a portion of navigation system 200, such as described further below. For example, ICD 110 may comprise processing circuitry configured to determine a location of a lead in the patient. In the illustrated example, navigation system 200 includes communication circuitry 202, processing circuitry 204, memory 206, a user interface 208, a power source 210, and impedance measurement circuitry 212. In an example, impedance measurement circuitry is coupled to a plurality of electrodes 214. Electrodes 214 may correspond to electrodes 106, electrodes 108, the housing electrode, electrodes on a delivery sheath or delivery tool, or other electrodes. Power source 210 may be a rechargeable or non-rechargeable battery, or another suitable source of power. Navigation system 200 may include additional components.

Electrodes 214 may comprise ring electrodes, hemispherical electrodes, coil electrodes, helical electrodes, ribbon electrodes, or other types of electrodes, or combinations thereof. Electrodes 214 may be the same type of electrodes or different types of electrodes. In some examples electrodes 214 may correspond to electrodes on the lead, and additionally or alternatively, may correspond to electrodes on the elongate tool or sheath. As such, a relative location of one or more electrodes 214 may be indicated, including a relative location of a component of the delivery system and/or a relative location of the lead. By using the techniques described herein, the delivery system may be navigated to more optimal location within the patient, which may allow for more efficient implantation of the lead.

Communication circuitry 202 includes any suitable hardware, firmware, software, or any combination thereof, for communicating with another device. For example, communication circuitry 202 may be configured to allow navigation system 200 to communicate with ICD 110, external device 130, or other devices or systems, in examples in which navigation system is not incorporated in such devices or system. Under the control of processing circuitry 204, communication circuitry 202 may receive downlink communications from and send uplink communications to another device with the aid of an antenna (not shown), which may be external, internal, or both. In some examples, communication circuitry 202 may communicate with a local external device, and processing circuitry 204 may communicate with a networked computing device via the local external device and a computer network. In some examples, other devices or systems, such as ICD 110 or external device 130, may include similar communication circuitry, such that there may be a communication link between devices, and data may be transferred, for example, from ICD 110 implanted in patient 10 to a computing device external to patient 10. In an example, communication circuitry 202 is configured to transmit the indication of the relative location of lead 102 to external device 130.

Processing circuity 204 may perform the techniques described herein for providing the indication of the relative location of the electrode in the patient. Processing circuitry 204 may include fixed function circuitry, programmable processing circuitry, or both. Processing circuitry 204 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 204 may include multiple components, such as any combination of one or more microprocessors, one or more controllers, one or more DSPs, one or more ASICs, or one or more FPGAs, as well as other discrete or integrated logic circuitry. The functions attributed to processing circuitry 204 herein may be embodied as software, firmware, hardware or any combination thereof.

Memory 206 includes computer-readable instructions that, when executed by processing circuitry 204, cause navigation system 200 and processing circuitry 204 to perform various functions attributed to navigation system 200 and processing circuitry 204 as described herein. Memory 206 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media. In some examples, memory 206 accumulates physiological data, such as sensed physiological signals, impedance signals or components thereof, or other data.

User interface 208 may include a display to present information to a user. In general, the user may interact with user interface 208. In an example, processing circuitry 204 may provide information (e.g., the indication, information about the relative location of the electrode, or information about a satisfactory ratio for positioning the lead) to user interface 208. In some examples, user interface 208 comprises a keyboard, keypad, touch screen, mouse, or the like, for receiving input from the user. User interface 208 may include a light or speaker, such as may be used to provide an indication or alert to the user. For example, if lead 102 becomes too close to an organ during navigation and placement of lead 102 in patient 10, processing circuitry 204 can control user interface 208 to, for example, initiate a blinking light or audible sound to alert the user of the relative location of lead 102. In an example, the systems and techniques described herein may alert the user if the heart or lung has been contacted or penetrated during the implant procedure. In an example, the systems and techniques described herein may alert (e.g., warn) the user when the heart or lung is about to be contacted or penetrated.

In general, a rapid or significant change in impedance, such as a sudden significant increase or decrease, may indicate a situation that may require further action by the physician. For example, a drop in the value of the measured impedance signal during the implant procedure may indicate that the electrode has encountered an air pocket in the substernal space. In an example, a change in the value of the measured impedance signal during the implant procedure may indicate that the lead has is about to, has contacted, or has entered the pericardial space. In an example, a sudden change in impedance may be indicative of the lead that the electrode is disposed on or has contacted, for example, the heart or the lungs. In response to a sudden change in the measured impedance signal, navigation system 200 may provide an indication (e.g., a warning, an alert, or any other indication to the user such as using user interface 208) to the user. The warning may be an attention-grabbing alert, such as a relatively loud noise, a blinking light, or another type of alert. For example, because the systems and techniques described herein may provide the indication of the relative location of the lead as the lead is being implanted, the physician may already know that a lead is in close proximity to the heart. For example, if the most distal electrode is determined to be close to the heart, and then there is a sudden change (e.g., increase) in the measured value of the impedance signal, then navigation system 200 may provide an alert to the physician indicating that the heart may have been penetrated. As such, the systems and techniques described herein may provide immediate feedback to a physician who, without such an indication, might not have had such information. By providing an alert to the user when there is an increased risk of contacting an organ (e.g., when the electrode is too close to the organ), navigation system 200 improves implant procedure safety. Or, for example, by using navigation system 200 as described herein, if the electrode (or lead or tool carrying the electrode) contacts an organ, the physician may be able to adjust the implant procedure accordingly.

In an example, processing circuitry 204 may determine a measurement of the impedance signal. The measurement may be a value as measured in ohms, degrees, or another measure of the impedance signal. Processing circuitry 204 may determine that the measurement of the impedance signal satisfies a criterion. For example, the criterion may correspond to a threshold value. The threshold value may be a minimum or maximum threshold value. If the measurement meets or exceeds the threshold, then processing circuitry 204 may provide a warning indication. In general, the systems and techniques described herein may help ensure that the electrode is placed in an appropriate location. If needed, a warning indication may be an indication designed to immediately warn or alert the user of a potential that the lead may be about to contact, for example, the lungs. Another criterion example may include a particular slope threshold of impedance over time, and the measurement of the impedance may be a slope of the signal. For example, if the measurement of the impedance signal changes too quickly, then that may be an indication the electrode is approaching, contacting, or has penetrated an organ. In other examples, the measurement of the impedance signal and the criterion are based on multiple elements, such as a function, or other information such as may be gathered from an imaging system. The warning indication may be provided to the user in response to the measurement of the impedance signal satisfying (e.g., meeting, crossing, exceeding) the criterion.

In some examples, multiple criteria may be used. For example, processing circuitry 204 may use a second criterion as confirmation of the measurement of the impedance signal satisfying the first criterion. In an example, the second criterion may be used to provide a second warning indication. The second warning indication may be more urgent (e.g., a red blinking light), where the first warning indication may be less urgent (e.g., a yellow blinking light). As such, the user may be provided information when there is a risk of contacting an organ (e.g., yellow light) and may be provided information when there has been contact or penetration of an organ (e.g., red light). By using the systems described herein, physicians may be better informed during the insertion procedure, such as to provide more optimal placement of the lead while maintaining safety for the patient (e.g., when a desired lead placement is in close proximity to the heart).

Navigation system 200 may include circuitry, such as may correspond to impedance measurement circuitry 212 in some examples, that may generate a waveform (e.g., a voltage waveform or a current waveform). The circuitry may deliver a signal via two or more of electrodes 214, and determine an impedance signal based on the delivery of the signal via the electrodes. The circuitry may be configured to generate one of a current or voltage signal, deliver the signal via a selected two or more of electrodes 214, and measure the resulting other of current or voltage. Processing circuitry 204 may determine an impedance signal based on the delivered current or voltage and the measured voltage or current. For example, such circuitry may be configured to inject a pulsatile waveform or a sinusoidal current waveform, such as of an amplitude below a threshold for capturing tissue.

In some examples, impedance measurement circuitry 212 may include one or more voltage or current sources, wave-shaping circuitry, switches, filters, amplifiers sample-and-hold circuitry, or analog-to-digital converters. As such, navigation system 200 may sample and hold a voltage value at a node of circuitry with the navigation system. The impedance signal may be filtered before the circuitry samples and holds the voltage value at the node, and the circuitry may also convert the sample to a digital signal. As such, impedance may be calculated based on the injected current amplitude and the sampled voltage.

Impedance measurement circuitry 212 generates a plurality of impedance signals. Impedance measurement circuitry 212 may be coupled to the one or more electrodes 214. Each of the impedance signals may indicate impedance proximate to an electrode (e.g., one of electrodes 214). Impedance measurement circuitry 212 may output the generated impedance signals to processing circuitry 204. Processing circuitry 204 identifies a first frequency component (such as may correspond to a cardiac contraction frequency) and a second frequency (such as may correspond to a respiration frequency) component for one or more of the impedance signals. Processing circuitry 204 may provide an indication of the relative location of the electrode in the patient based on the first and second frequency components.

Figure 3:
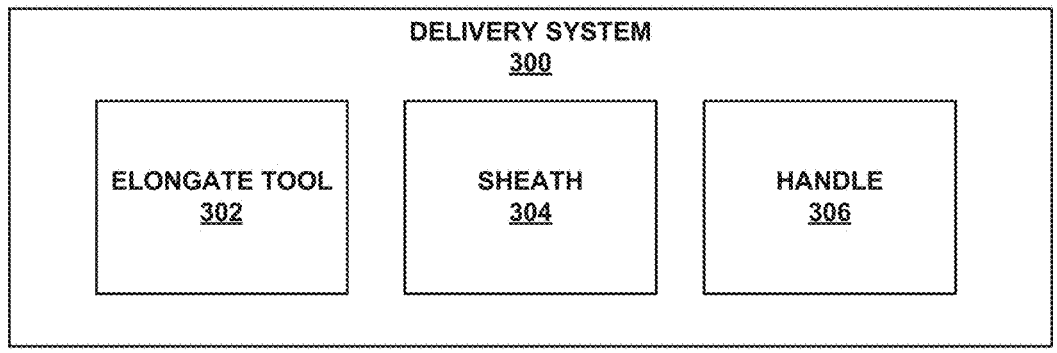
FIG. 3 is a functional block diagram illustrating an example configuration of a delivery system.

FIG. 3 is a functional block diagram illustrating an example configuration of delivery system 300. Delivery system 300 includes, for example, an implant tool. The implant tool may include elongate tool 302, sheath 304, and handle 306. By using delivery system 300 with navigation system 200, lead 102 may be placed such that a therapy vector between a defibrillation electrode on the lead and a housing or can electrode is substantially across the ventricle of the heart, or in another desired location within the substernal space, such as described further below. In general, delivery system 300 is for implanting a medical electrical lead (e.g., lead 102) in a substernal space of a patient.

Figure 4:
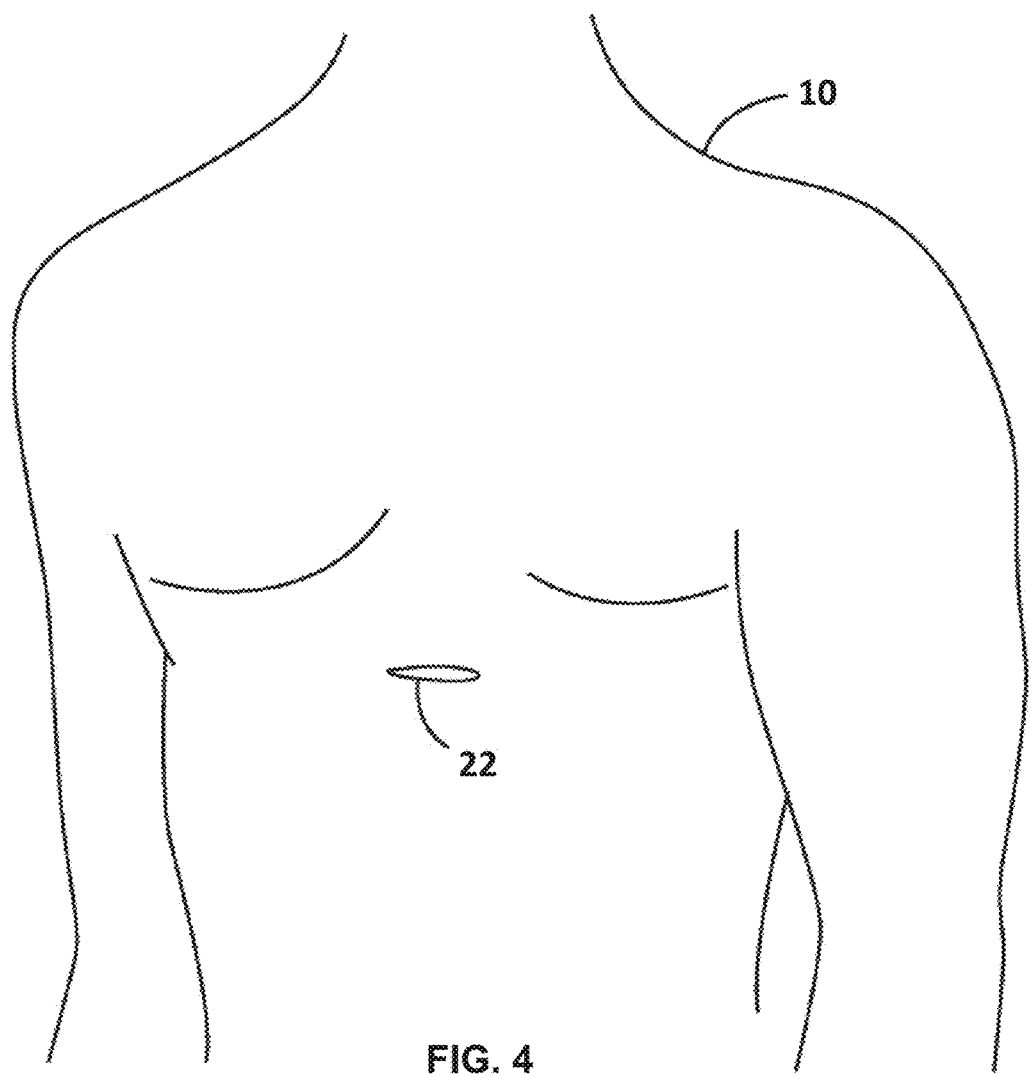
FIG. 4 is a partial perspective view that illustrates a portion of a technique of implanting a lead.

FIG. 4 is a partial perspective view that illustrates a portion of a technique of implanting a lead. For example, for patient 10, an incision 22 is made on the skin or tissue adjacent to or below the xiphoid process (also referred to as "subxiphoid") to form an access point sized for passage of delivery system 300, or additionally or alternatively, lead 102 to the substernal space. The access point may also be formed at the notch (not shown) that connects the xiphoid process to the sternum. In other examples, the substernal space may be accessed through the manubrium.

FIG. 5A is a partial perspective view that illustrates a portion of a technique of implanting a lead (such as lead 102). For example, elongate tool 302 (not shown) within sheath 304 may be used to implant a lead to achieve a desired location, such as over a silhouette of heart 12. Longitudinal axis 308 of elongate tool 302 and sheath 304 are shown. In some examples, a desired location within the substernal space may include lead 102 being positioned with one or more therapy or sensing vectors. Delivery system 300 may be coupled (e.g., shown with dotted line 142) to an external device 140. Such coupling may include, for example, being electrically coupled, communicatively coupled, wirelessly coupled, and the like. In some examples, external device 140 may communicate with other devices, like described with respect to external device 130. In some examples, external device 140 is a mapping unit (e.g., a relative location mapping unit, such as may include a display for a user). In some examples, the lead is connected to external device 140 for navigation (e.g., a proximal connector of the lead may provide such a connection). Elongate tool 302 and/or sheath 304 may include one or more electrodes. The one or more electrodes may be coupled, such as via conductors and one or more connectors, to external unit 140. As such, as delivery system 300 is tunneled into the patient, the navigation guidance techniques described herein may be used with the one or more electrodes of the delivery system.

External device 130 or 140 may comprise all or part of navigation system 200. In such examples, the external device 130 or 140 may be electrically connected to electrodes on tool, sheath, and/or lead 102, and generate impedance signals for use in navigation according to the techniques of this disclosure. In some examples, external device 140 may be a separate external device from external device 130, which may generally be used as a programmer for an ICD, for example, when implanted. In some examples, if the ICD is being used as at least a portion of a navigation system (e.g., ICD comprising navigation system 200), then the ICD may not yet be implanted in the patient, but is nevertheless connected to the lead during navigation to facilitate delivering a voltage or current signal via electrodes to determine the impedance signal.

FIG. 5B is a perspective view that illustrates a portion of a lead delivery system 300A. System 300A is one example of delivery system 300 of FIG. 3. As such, for example, sheath 304A is an example of sheath 304. For system 300, other configurations, shapes, or sizes may be used for various elements. In some examples, one or more electrodes 316 may be positioned on the sheath 304A, on the elongate tool 302A, or on both. The electrodes 316 may be used in conjunction with, or as a substitute for a radiopaque marker element 314, to facilitate mapping of the location of the delivery system 300A within the substernal implant location. Although electrodes 316 are illustrated in the example of FIG. 5B as being positioned on distal portions of sheath 304A and elongate tool 302A, other locations for positioning electrodes 316 may be used. For example, one or more electrodes may be positioned on a proximal portion of portions of the lead delivery system, on a medial portion, at any circumferential position, or any combination thereof. The electrodes 314 may be electrically coupled to a location mapping unit, which may be an external device (e.g., external device 140). Initially, elongate tool 302A may be disposed within sheath 304A. With elongate tool 302A inside of sheath 304A, the user may guide the delivery system using handle 306A to an appropriate position within the substernal space, for example. In some examples, impedance signals may be generated, such as proximate to electrode(s) 316, while guiding the delivery system to the appropriate position within the substernal space. Sheath 304A may be implanted at the appropriate position. As described above, one or both of elongate tool 302A or sheath 304A may include one or more electrodes, and as such, will also include a proximal connector for connecting to an external device (e.g., external device 140), such as may comprise navigation system 200. Navigation system 200 being coupled to one or more electrodes (e.g., 214, 316, or other electrodes) allows the user to safely implant the navigation system and the lead.

Once sheath 304A is in a suitable location, elongate tool 302A may be removed. The lead (e.g., lead 102) may be advanced through sheath 304A (e.g., an inner stylet may be used to provide stiffness for the implantation procedure). The lead may be coupled to the navigation system for guidance. Additionally or alternatively, the lead may be coupled to the ICD that incorporates a portion of the navigation system.

Some implant systems may not involve sheath, and instead may include a tool that is coupled to and alongside the distal end of the lead, and used to push the distal end to the desired location. In this case, either the tool (if it has electrodes) or the lead may be connected to the impedance circuitry in the navigation system.

In some examples, elongate tool 302A may include a pre-biased curvature 310 that is formed along a length of the body of elongate tool 302A. As shown in FIG. 5B, the pre-biased curvature 310 is configured such that the segment of elongate tool 302A adjacent to distal end 312 is curved to orient the distal portion in a non-parallel plane relative to the plane defined by the proximal portion. The angle of curvature of the pre-biased curvature is predicated on orienting the section of elongate tool 302A that is proximal to distal end 312 at an angle that is substantially perpendicular to the sternum of the patient while the rest of elongate tool 302A is generally parallel to the sternum of the patient. For example, the pre-biased curvature 310 is configured to have a bend that orients the distal end 312 at an angle that is greater than 5 degrees relative to a first plane defined along a central axis of the proximal portion of the elongate tool 302A.

The distal end 312 may be configured to provide a tactile signal in response to contact with tissue, bone, or other anatomical features along a pathway from the access point into the substernal space of the patient to a desired implant location. For example, the pre-biased curvature 310 may be oriented such that the distal end 312 is placed in contact with the sternum, or more particularly the sternebrae. The curvature may maintain relative spacing between sheath 304A and the sternum. In other examples, curvature 310 may not be required, and as such, elongate tool 302A may not have a curved distal end. The distal end 312 may contact the various bones along the ribcage or at the fusion point between the ribs and the sternum or with the sternum itself as the elongate tool 302A is advanced during the implantation. Responsive to the contact between the elongate tool 302A and the patient, distal end 312 creates a tactile signal that provides an indication of the position of the distal end 312 relative to the patient. Such a tactile signal may supplement the impedance mapping techniques described herein.

In some embodiments, a radiopaque marker element 314 may be disposed on the elongate tool 302A and/or sheath 304A. In the illustrative embodiment of FIG. 5B, for example, the element 314 is depicted overlaying a segment of the distal end 312. Nevertheless, it should be understood that the element 314 may overlay or coat any other section or sections of elongate tool 302A or may alternatively overlay the entire elongate tool 302A. Element 314 may be formed from a band of radiopaque material that is coupled to the distal end 312 through any suitable mechanism. In other examples, the distal-most portion of elongate tool 302A may be formed from a radiopaque material. The radiopaque material may include a compound, such as barium sulphate, that is visible through a fluoroscopic imaging procedure, although, this may not be required when using the navigation system to safely implant the delivery system or the lead. In use, the marker element 314 may provide a visual depiction or image of the distal end 312, which may supplement use of the navigation system.

Figure 6:
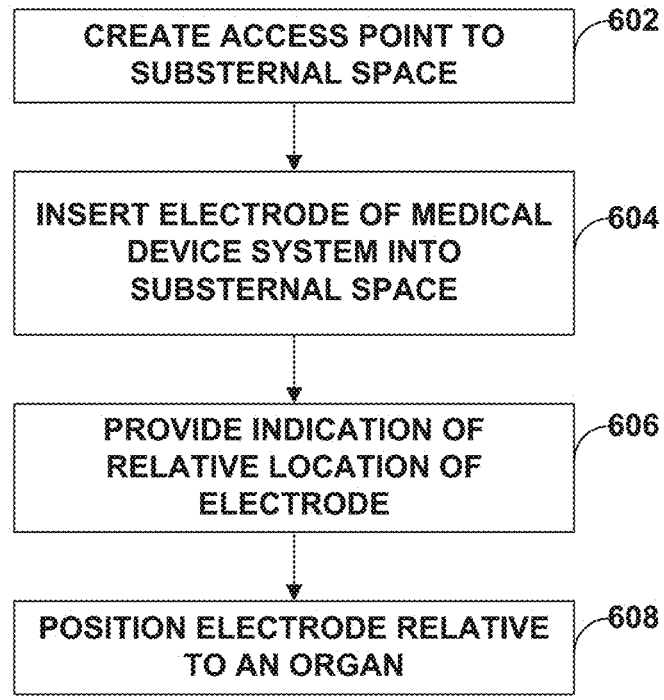
FIGS. 6 and 7 are flow charts depicting a method of implanting a lead according to some examples of this disclosure.

FIG. 6 is a flow chart depicting a method of implanting a lead according to some examples of this disclosure. The example method may be performed in part by a clinician and in part by any one or more devices embodying a navigation system, as described herein. According to the example method, a clinician creates an access point into the substernal space, such as the incision 22 made on the skin or tissue adjacent to or below the xiphoid process as described with respect to FIG. 4 (602).

In an example, delivery system 300 is provided for facilitating the lead 102 to the target location. The clinician inserts the electrode into the substernal space (604). As described herein, the electrode may be disposed on a medical lead, or on a sheath or tool of a delivery system. Positioning the electrode, such as positioning lead 102 that includes the electrode, may include using the indication of the relative location the electrode as described herein. In an example, during the advancing of the delivery system, the distal end of elongate tool 302 is navigated in direct contact or close proximity with the sternum. In some examples, a fluid may be delivered during the advancing of the delivery system into the substernal space. For example, the delivery system may deliver an analgesic agent or a contrast solution or any other suitable fluid. An imaging procedure may be performed to obtain an image of a segment of the delivery system, although this may not be required.

Navigation system 200, e.g., user interface 208 of navigation system 200, as controlled by processing circuitry 204, provides an indication of the relative location of one or more electrodes, e.g., on lead 102 or on the elongate tool of the delivery system (606). The indication may correspond to a location of the electrode relative to one or more organs in the patient. The indication may change over time or space, such as because impedance morphology may change at different locations of the lead relative to the heart. By using the navigation system, a better placement of the lead may be achieved. For example, as lead 102 is being positioned or adjusted, a distance from the electrode to the organ may change. As such, the clinician positions the electrode at a suitable location, using the indication, relative to the heart and the lung of the patient (608). This positioning may, in some examples, be performed while lead 102 is within sheath 304.

As such, for example, a user may receive an indication of the relative location of the lead in the patient before removing sheath 304. In some examples, portions of the delivery system may not be fluoro-visible, and the techniques and systems described herein may not require medical imaging (e.g., fluoroscopic, X-ray, CT, or the like) for safe lead placement.

In some examples, sheath 304 has one or more windows, such as cut-outs in the sheath. The one or more windows may correspond to electrodes on the lead, and may be configured to expose the electrodes on the lead so that the impedance signal generated using electrodes may adequately indicate the relative location of the electrodes to one or more patient structures. For example, as the lead is being positioned by the user, the user may receive indications over time as the location of the lead changes, such as to find an appropriate final implant location. In an example, as the lead is being positioned by the user, the windows may be rotated relative to the electrodes to alter the radial direction of the exposed electrical field (e.g., thereby altering a direction relative to the lead from which components of the impedance signal are obtained), such as may provide additional directional guidance for the user. The navigation system allows the user to make a tunnel in the substernal space and then determine where to position the lead, such as based on the indication of the relative location of the lead. Additionally or alternatively, the navigation system 200 allows the user to determine where to position the lead while such tunneling is occurring, such as by using real-time indications of the relative location of the lead in the substernal space. Furthermore, the navigation system may provide the user with a confirmation of the appropriate location after the user has decided on a lead placement location.

In some examples, the indication may be the confirmation that lead 102 is positioned at the appropriate location. The appropriate location may include a relative cranial-caudal location, such as along axis 308 as shown in FIG. 5A. The appropriate location may include a relative left-right lateral location, such as to position a defibrillation electrode over the patient's heart, as the heart (e.g., the left ventricle) may not be symmetrically centered on the patient's midline. The appropriate location may be a relative ventral-dorsal location, such as to position the lead closer or further from the patient's sternum. The appropriate location may include achieving appropriate vectors, such as described above. Any combination of the preceding locations or other locations may be achieved by using the techniques herein. The indication of the relative location of electrodes on lead 102 may be used to determine or confirm the appropriate implant location.

In some examples, the indication the navigation system provides to the user may be an indication that comprises feedback, such as real-time feedback to the user. For example, the real-time feedback may indicate that the lead would be more appropriately placed more cranially. Another example of an indication includes an alert that the lead is too close to an organ, such as if the impedance meets or crosses a threshold or if the ratio of respiration impedance to cardiac impedance meets or crosses a threshold.

Figure 7:
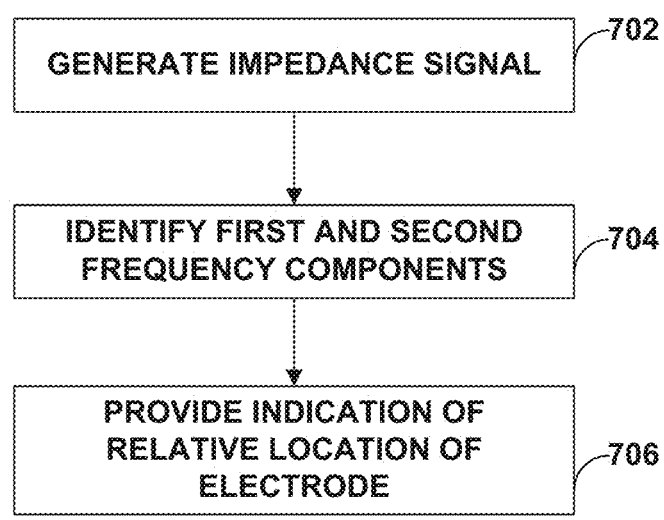

FIG. 7 illustrates an example method for providing an indication of the relative location of an electrode. The example method may be performed by any one or more devices embodying a navigation system 200, e.g., by processing circuitry 204 of the navigation system, as described herein. Impedance measurement circuitry 212 may generate an impedance signal (702). In an example, the impedance signal may be visually depicted as in the graphs of FIG. 8C, and as described below. The impedance signal may correspond to a real impedance or a reactive impedance. In general, impedance may be represented as a complex quantity, such as including a real part (e.g., resistance) and an imaginary part (e.g., reactance). Processing circuitry 204 may identify first and second frequency components from the impedance signal (704). The first and second frequency components may correspond to the cardiac contraction signal (e.g., cardiac contraction frequency) and the respiration signal (e.g., the respiration frequency), respectively.

Each of the first and second frequency components may have different characteristics at a particular time. For example, the frequency components may have different frequencies, different amplitudes, different wavelengths, or other differences. The characteristic may change as the electrode moves within the substernal space, or may change due to a change in the patient's physiological state. Processing circuitry 204 may determine a characteristic for each frequency component (e.g., a first characteristic for the first frequency component and a second characteristic for the second frequency component). In some examples, the characteristic is an amplitude for each of the frequency components. In some examples, the characteristic of the first and second frequency components is a power in Fourier space, based on a function such as may include a weighting factor, or based on other signal characteristics.

Processing circuitry 204 may determine a relationship between the first and second characteristic (e.g., between the first and second amplitudes). In some examples, the relationship is a ratio. The ratio may be a ratio of the first characteristic to the second characteristic. The ratio may be a dimensionless quantity (e.g., such as the Y-axis in the examples of FIGS. 10C and 10D). As described below, FIG. 10D corresponds to the caudal position of the lead as in FIGS. 9C and 9D, and the vector including electrode 118B has a relatively higher ratio than the other electrodes. As such, electrode 118B, in this example, is relatively closer to the lungs, while electrodes 116A, 116B, and 118A are relatively closer to the heart (e.g., "over the silhouette" of the heart). In some examples, the relationship may be based on a function such as may include a weighting factor, or based on other relationships between the first and second characteristics.

Processing circuitry 204 may provide the indication of the relative location of the electrode based on the first and second frequency components (e.g., based on the relationship between the frequency components) (706). For example, a relatively higher ratio, such as electrode 118B in the examples of FIGS. 9D and 10D, may correspond to an electrode location that is relatively closer to the lungs than the heart. In indication of the relative location of the electrode may be based on the relationship. By using the indication of the relative location of the lead based on the first and second frequency components during the placement procedure, post-placement vectors may be predicted. For example, the indication may be used to aide in selecting vectors for pacing or sensing, or therapy. As such, by using the systems and techniques described herein, better lead placement may be achieved, such as may provide better lead stability within the patient for the life of the implant.

In some examples, filtering may be performed, such as by the processing circuitry, after generating the impedance signal. A Fourier transform may be performed on the impedance signal, impedance peaks may be identified, filters may be applied, or other processing techniques may be used. In some examples, a 10-hertz low pass filter is applied, and then a Fourier transform is performed.

In some examples, the first frequency component includes values of about 0.15 hertz to about 0.45 hertz, such as about 0.3 hertz (e.g., about 18 breaths per minute). In some examples, the second frequency component includes values of about 0.66 hertz to about 1.66 hertz, such as about 1.0 hertz (e.g., about 60 heart beats per minute). As such, the first and second frequency components may be distinguished for determining the relationship therebetween.

In general, the systems and techniques described herein may be using with other types of leads alternatively or in addition to substernally implanted leads. By using the systems and techniques herein to supplement the delivery procedure of the lead, safer tunneling of the lead and the delivery system may be achieved. In other examples, the systems and techniques may be used as a diagnostic tool for respiration or cardiac monitoring (e.g., such as EKG monitoring).

FIGS. 8A and 8B illustrate examples of substernal space locations in a patient. FIG. 8A is a medical image of a substernal space including heart 12A. FIG. 8B is pictorial graphic of a substernal space including heart 12B. In each of FIGS. 8A and 8B, electrode locations 24 at locations 1 through 20, as illustrated, such as relative to hearts 12A and 12B. FIG. 8C illustrates graphs of examples including impedance signals for different locations in a substernal space of a patient. For example, in the graph for location 11-12 on the left, the total impedance and phase shift are dominated by the heart-beat, as the impedance signal may be seen as corresponding to the left ventricular pressure signal. In the graph for location 19-20, on the other hand, the total impedance and the phase shift are dominated by respiration. As such, an electrode at location 11-12 may be relatively closer to the heart than the lungs, while an electrode at location 19-20 may be relatively closer to the lungs than the heart. In some examples, locations other than 1-20 may be used, such that a relative location of an electrode may be determined for anywhere in the substernal space. In some examples, the phase shift measure may be indicative of how, for example, a current signal lags a voltage signal. In some examples, measures such as complex impedance, real impedance, phase shift (e.g., also may be referred to as "phase factor"), or total impedance (which may all be related to one another), may include components of different signals. For example, these or other measures may be dominated by, for example, respiration, when the measurement electrode is relatively closer to the lungs than the heart.

Figure 9A:
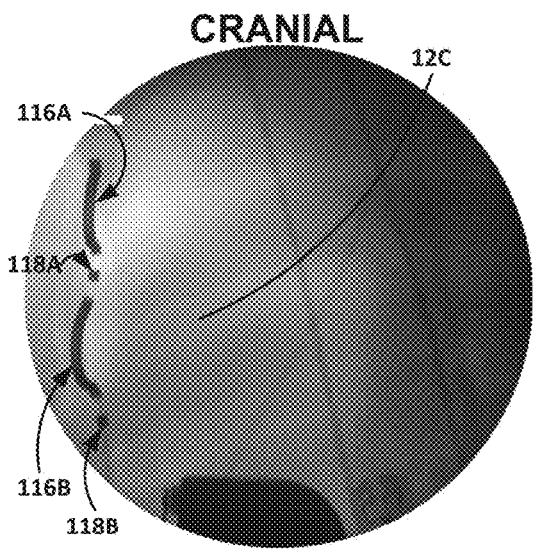
FIGS. 9A-9D illustrate examples of leads placed in substernal spaces.
Figure 9B:
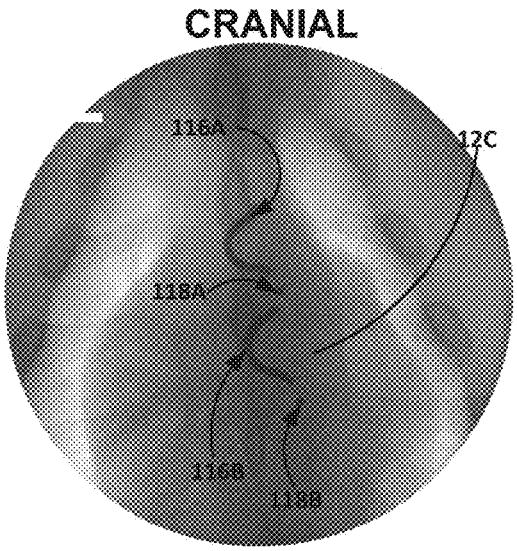
Figure 9C:
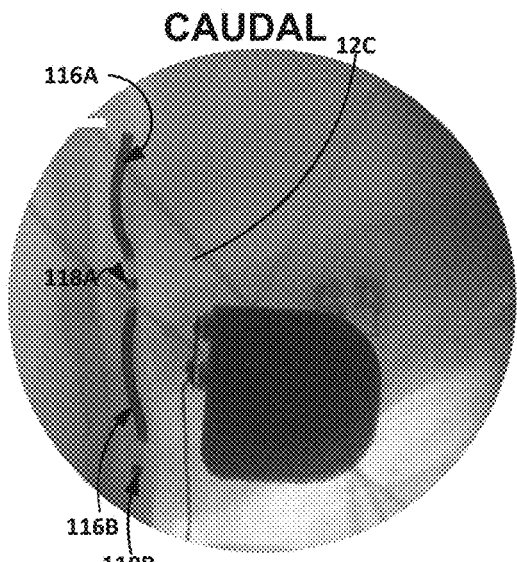
Figure 9D:
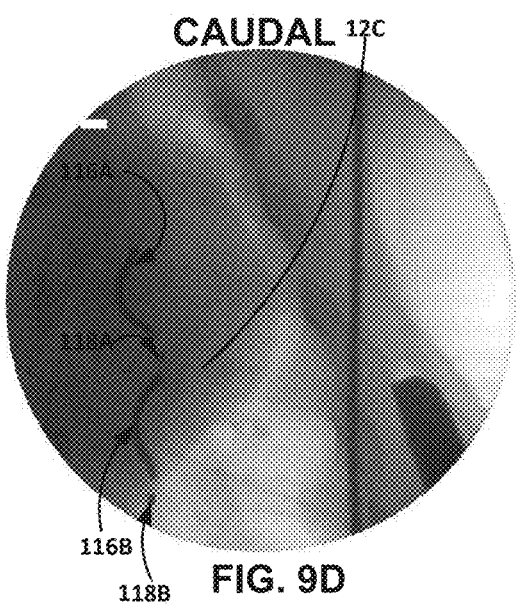

FIGS. 9A-9D illustrate examples of leads placed in substernal space locations in a pig model with a heart 12C. FIGS. 9A and 9B are views of the lead with defibrillation electrodes 116A and 116B, and sensing electrodes 118A and 118B, such as in a cranial midline position. FIGS. 9C and 9D are view of the lead with electrodes 116A, 116B, 118A, and 118B, such as in a caudal midline position. These examples of lead locations are discussed further with respect to FIGS. 10A-10E.

FIG. 10A illustrates bar graphs of minimum impedance 120 (left bar), mean impedance 122 (middle bar), and maximum impedance 124 (right bar) for vectors between lead electrodes 116A, 116B, 118A, 118B and a housing electrode (e.g., also referred to as "can electrode," "can," or "active can electrode (ace)"). FIG. 10A corresponds to the caudal position of the lead as in FIGS. 9C and 9D.

FIG. 10B illustrates bar graphs of minimum impedance 120 (left bar), mean impedance 122 (middle bar), and maximum impedance 124 (right bar) for vectors between lead electrodes 116A, 116B, 118A, 118B and the can. FIG. 10B corresponds to the cranial position of the lead as in FIGS. 9A and 9B. FIGS. 10A and 10B each include an 8 kilohertz (using one type of bioimpedance module) and 12 kilohertz (using another type of bioimpedance module) set of impedance bars for each vector. By using two types of modules with two different frequencies, measurement equivalency may be seen across different systems. Navigation system 200 may comprise these 8 and 12 kilohertz or other amplifiers, such as may be implemented on external device 130. FIGS. 10A and 10B illustrate the ability of navigation system 200 to measure impedance in the substernal space, such as to determine the relative location of an electrode in the substernal space.

Figure 10C:
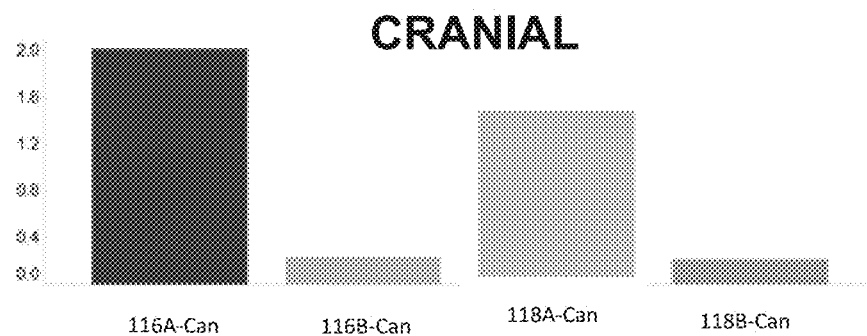
Figure 10D:
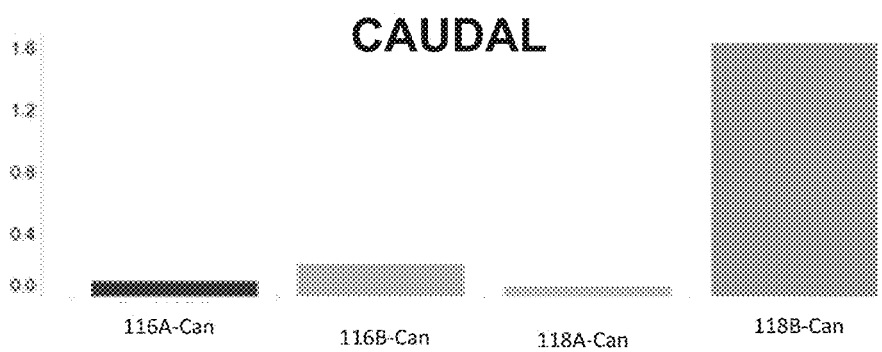

FIG. 10C illustrates a bar graph of the ratio of respiration impedance to cardiac impedance for four vectors (e.g., 116A to can on the left, 116B to can second from left, 118A to can third from left, and 118B to can on right). FIG. 10C corresponds to the cranial position of the lead as in FIGS. 9A and 9B, and vectors including electrodes 118A and 116A have relatively higher ratios than vectors including electrodes 118B and 116B. As such, 118A and 116B, in this example, are relatively closer to the lungs than the heart, such as may be seen in FIGS. 9A and 9B. FIG. 10D illustrates a bar graph of the ratio of respiration impedance to cardiac impedance for four vectors (e.g., 116A to can on the left, 116B to can second from left, 118A to can third from left, and 118B to can on right). FIG. 10D corresponds to the caudal position of the lead as in FIGS. 9C and 9D, and the vector including electrode 118B has a relatively higher ratio than the other electrodes. As such, electrode 118B, in this example, is relatively closer to the lungs, while electrodes 116A, 116B, and 118A are relatively closer to the heart (e.g., "over the silhouette" of the heart). The impedance ratio between the first and second components, as illustrated herein, may correlate with lead location in the substernal space.

Figure 10E:
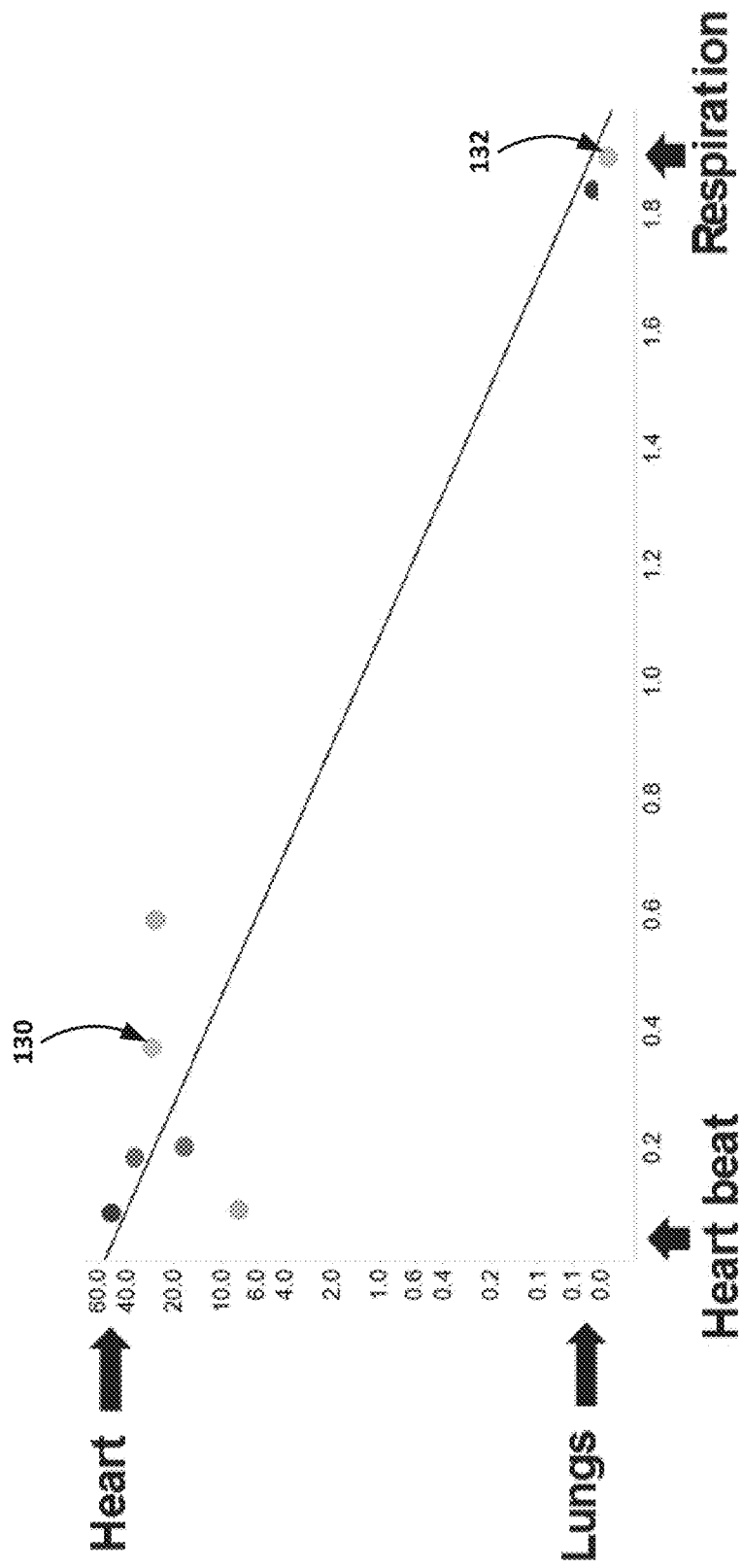

FIG. 10E illustrates a graph of impedance ratio to medical imaging measurements for various electrode locations. The impedance ratio (X-axis), such as described herein, is larger for point 132 than for point 130. In an example, both points 130 and 132 represent the impedance ratio for a vector between electrode 118B, where point 130 may correspond to a more cranial location (e.g., as in FIGS. 9A and 9B, and point 132 may correspond to a more caudal location (e.g., as in FIGS. 9C and 9D), such as measured at different times. The Y-axis corresponds to a ratio of (1) a shortest distance from the electrode to the lung to (2) the shortest distance from the electrode to the epicardial surface of the heart. These two distances may be measured using CT reconstruction. In this example, the distances are measured in units of millimeters. As such, the impedance ratio may correlate with the relative distance of the electrode to the heart or the lungs.

In an example, user interface 208 includes a display. The display may provide any type of visual information, such as similar to that of FIGS. 8A-8C, 9A-9D, 10A-10E, or any combination thereof. The display may provide a visual representation (e.g., a numeral, a bar chart, or another representation) of the impedance proximate to an electrode or multiple electrodes, including a graph showing changes over time. In an example, the display may provide graphs and tables other than those shown in the figures. In an example, user interface 208 may provide additional data, such as data about correlating distance from one or more organs. In an example, a pictorial guide, such as a lateral or top-down visual of the leads may be provided. Such a pictorial guide may indicate the approximate location of the lead in the chest cavity. In some examples, the processing circuitry may provide an indication of the relative location of the electrode or of a satisfactory impedance measurement. Additionally or alternatively, user interface 208 may provide such indications, in some examples.

By using the techniques and systems described herein, lead performance may be increased as the lead may be placed at a more optimal location for therapeutic stimulation. Therapies, such as defibrillation or anti-tachycardia pacing, may be improved, as well as sensing abilities and battery life. The indication of the relative location of the electrode may be used to avoid being too close to an organ, such as in terms of electrical proximity (e.g., based on the impedance signal). Further, a better map of the substernal space, via impedance information, may be provided to a user, such as a physician.

The following numbered clauses demonstrate one or more aspects of this disclosure.

Clause 1: In one example, a method comprises generating, by impedance measurement circuitry coupled to an electrode, an impedance signal indicating impedance proximate to the electrode; identifying, by processing circuitry, a first frequency component and a second frequency component of the impedance signal; and providing, by the processing circuitry and to a user, an indication of a location of the electrode in a patient based on the first frequency component and the second frequency component.

Clause 2: In some examples of the method of clause 1, the method further comprises determining, by the processing circuitry, a first characteristic of the first frequency component and a second characteristic of the second frequency component, wherein providing the indication of the location of the electrode in the patient comprises providing the indication of the location of the electrode in the patient based on the first characteristic and the second characteristic.

Clause 3: In some examples of the method of clause 2, the method further comprises determining, by the processing circuitry, a relationship between the first characteristic and the second characteristic, wherein providing the indication of the location of the electrode in the patient comprises providing the indication of the location of the electrode in the patient based on the relationship between the first characteristic and the second characteristic.

Clause 4: In some examples of the method of clause 3, the relationship comprises a ratio of the first characteristic to the second characteristic.

Clause 5: In some examples of the method of clause 2 or 3, the first frequency component corresponds to a cardiac contraction frequency, the first characteristic comprises an amplitude of the first frequency component, the second frequency component corresponds to a respiration frequency, and the second characteristic comprises an amplitude of the second frequency component.

Clause 6: In some examples of the method of any of clauses 2, 3, or 5, the first characteristic and the second characteristic comprise one of an amplitude, frequency, wavelength, a power in Fourier space, or an intensity in the Fourier space.

Clause 7: In some examples of the method of any of clauses 1-6, the first frequency component corresponds to a cardiac contraction frequency and the second frequency component corresponds to a respiration frequency, and wherein providing the indication of the location of the electrode in the patient comprises providing the indication of the location of the electrode relative to at least one of a heart or lungs of the patient.

Clause 8: In some examples of the method of any of clauses 1-7, the method further comprises providing the indication of the location of the electrode comprises providing an indication of the location of the electrode relative to at least one of: a sternum; a heart; a lung; or a portion of the heart or the lung.

Clause 9: In some examples of the method of any of clauses 1-8, providing the indication of the location of the electrode in the patient includes providing an indication of at least one of: a relative cranial-caudal location of the electrode, a relative left-right lateral location of the electrode, or a relative ventral-dorsal location of the electrode.

Clause 10: In some examples of the method of any of clauses 1-9, the method further comprises generating the impedance signal, identifying the first and second frequency components, and providing the indication of the location periodically over time as the location changes.

Clause 11: In some examples of the method of any of clauses 1-10, the method further comprises generating, by the impedance measurement circuitry, a plurality of impedance signals, each of the impedance signals indicating impedance proximate to a respective one of a plurality of electrodes, the plurality electrodes coupled to the impedance measurement circuitry and including the electrode; identifying, by the processing circuitry and for each of the plurality of impedance signals, the first and second frequency components; and providing, by the processing circuitry and for at least one of the electrodes, an indication of the location of the electrode in the patient based on the first and second frequency components of the respective impedance signal.

Clause 12: In some examples of the method of clause 11, providing the indication of the location of the at least one of the plurality of electrodes in the patient comprises providing the indication of the location of the at least one of the plurality of electrodes based on the location of at least one other electrode of the plurality of electrodes.

Clause 13: In some examples of the method of clause 11 or 12, providing the indication of the location of the at least one of the plurality of electrodes in the patient comprises providing the indication of the location of the at least one of the plurality of electrodes based on the location of at least one other electrode of the plurality of electrodes based on a comparison of the first and second frequency components for the plurality of impedance signals.

Clause 14: In some examples of the method of any of clauses 1-13, a range of frequency values of the first frequency component includes values of about 0.15 hertz to about 0.45 hertz, and a range of frequency values of the second frequency component includes values of about 0.66 hertz to about 1.66 hertz.

Clause 15: In some examples of the method of any of clauses 1-14, providing the indication of the location of the electrode in the patient includes determining the location of the electrode without fluoroscopic imaging information.

Clause 16: In some examples of the method of any of clauses 1-15, the electrode is positioned on a medical lead configured for implantation within a substernal space of the patient.

Clause 17: In some examples of the method of any of clauses 1-16, the electrode is positioned on an implant tool configured for advancement into a substernal space of the patient, the implant tool defining a channel configured to receive a medical lead for implanting the medical lead in the substernal space.

Clause 18: In some examples of the method of any of clauses 1-17, the method further comprises determining, by the processing circuitry, that a measurement of the impedance signal satisfies a criterion.

Clause 19: In some examples of the method of any of clauses 1-18, the method further comprises providing, by the processing circuitry and to the user, a warning indication in response to determining that the measurement satisfies the criterion.

Clause 20: In some examples, a medical device system comprises: an electrode; impedance measurement circuitry coupled to the electrode, the impedance measurement circuitry configured to generate an impedance signal indicating impedance proximate to the electrode; and processing circuitry configured to: identify a first frequency component and a second frequency component of the impedance signal; and provide an indication of a location of the electrode in a patient based on the first frequency component and the second frequency component.

Clause 21: In some examples of the medical device system of clause 20, the medical device system further comprises a substernally implantable medical lead, the electrode disposed on the substernally implantable medical lead.

Clause 22: In some examples of the medical device system of clause 20 or 21, the processing circuitry is configured to determine a first characteristic of the first frequency component and a second characteristic of the second frequency component, wherein the processing circuitry is configured to provide the indication of the location of the electrode in the patient based on the first characteristic and the second characteristic.

Clause 23: In some examples of the medical device system of clause 22, the processing circuitry is configured to determine a relationship between the first characteristic and the second characteristic, wherein the processing circuitry is configured to provide the indication of the location of the electrode in the patient based on the relationship between the first characteristic and the second characteristic.

Clause 24: In some examples of the medical device system of clause 22 or 23, the first frequency component corresponds to a cardiac contraction frequency, the first characteristic comprises an amplitude of the first frequency component, the second frequency component corresponds to a respiration frequency, and the second characteristic comprises an amplitude of the second frequency component, and wherein the processing circuitry is configured to determine the amplitude of the first frequency component and the amplitude of the second frequency component.

Clause 25: In some examples of the medical device system of clause any of clauses 22-24, the first characteristic and the second characteristic comprise one of an amplitude, frequency, wavelength, or an intensity in the Fourier space.

Clause 26: In some examples of the medical device system of clause 23, the relationship comprises a ratio of the first characteristic to the second characteristic, and wherein the processing circuitry is configured to determine the ratio.

Clause 27: In some examples of the medical device system of any of clauses 20-26, the first frequency component corresponds to a cardiac contraction frequency and the second frequency component corresponds to a respiration frequency, and wherein the processing circuitry is configured to provide the indication of the location of the electrode in the patient relative to at least one of a heart or lungs of the patient.

Clause 28: In some examples of the medical device system of any of clauses 20-27, the processing circuitry is configured to provide the indication of the location of the electrode relative to at least one of: a sternum; a heart; a lung; or a portion of the heart or the lung.

Clause 29: In some examples of the medical device system of any of clauses 20-28, the processing circuitry is configured to provide an indication of at least one of: a relative cranial-caudal location of the electrode, a relative left-right lateral location of the electrode, or a relative ventral-dorsal location of the electrode.

Clause 30: In some examples of the medical device system of any of clauses 20-29, the impedance measurement circuitry is configured to generate the impedance signal, wherein the processing circuitry is configured to identify the first and second frequency components, and wherein the processing circuitry is configured to provide the indication of the location periodically over time as the location changes.

Clause 31: In some examples of the medical device system of any of clauses 20-30, the processing circuitry is configured to provide the indication of the location of the electrode in the patient without fluoroscopic imaging information.

Clause 32: In some examples of the medical device system of any of clauses 20-31, the electrode is positioned on an implant tool configured for advancement into a substernal space of the patient, the implant tool defining a channel configured to receive a medical lead for implanting the medical lead in the substernal space.

Clause 33: In some examples of the medical device system of any of clauses 20-32, the medical device system further comprises a lead, wherein the electrode is disposed on the lead, and wherein a proximal end of the lead includes a connector to connect the lead to a medical device.

Clause 34: In some examples of the medical device system of clause 33, the medical device system further comprises a plurality of electrodes disposed on the lead, wherein the impedance measurement circuitry is configured to generate a plurality of impedance signals, each of the impedance signals indicating impedance proximate to a respective one of the plurality of electrodes, the plurality electrodes coupled to the impedance measurement circuitry and including the electrode.

Clause 35: In some examples of the medical device system of clause 34, the processing circuitry is configured to identify for each of the plurality of impedance signals, the first and second frequency components, and wherein the processing circuitry is configured to provide for at least one of the electrodes, an indication of the relative location of the electrode in the patient based on the first and second frequency components of the respective impedance signal.

Clause 36: In some examples of the medical device system of any of clauses 20-35, the processing circuitry is configured to determine that a measurement of the impedance signal satisfies a criterion.

Clause 37: In some examples of the medical device system of clause 36, the processing circuitry is configured to provide a warning indication to the user in response to determining that the measurement satisfies the criterion.

Clause 38: In some examples, a medical device system comprises: an electrode; impedance measurement circuitry coupled to the electrode, the impedance measurement circuitry configured to generate an impedance signal indicating impedance proximate to the electrode; and processing circuitry configured to: identify a first frequency component of the impedance signal corresponding to a cardiac contraction frequency and a second frequency component of the impedance signal corresponding to a respiration frequency; determine a first amplitude of the first frequency component and a second amplitude of the second frequency component; determine a relationship between the first amplitude and the second amplitude; and provide an indication of a location of the electrode in a patient based on the relationship.

Clause 39: In some examples of the medical device system of clause 38, the relationship comprises a ratio of the second amplitude to the first amplitude.

Clause 40: In some examples of the medical device system of clause 38 or 39, the medical device system further comprises a user interface configured to provide an indication that the electrode is closer to a lung of the patient than a heart of the patient when the ratio is relatively larger, and configured to provide an indication that the electrode is closer to a heart of the patient than the lung of the patient when the ratio is relatively smaller.

Clause 41: In some examples of the method of clause 17, the implant tool comprising a sheath including a window corresponding to the electrode, the method further comprises rotating the window to alter an exposed signal field.

Various examples have been described. These and other examples are within the scope of the following claims.

What is claimed is:

1. A method for indicating a location of an electrode in a patient, the method comprising:
   generating, by impedance measurement circuitry coupled to the electrode, an impedance signal indicating impedance proximate to the electrode;
   identifying, by processing circuitry, a first frequency component and a second frequency component of the impedance signal; and
   providing, by the processing circuitry and to a user, an indication of the location of the electrode in the patient based on the first frequency component and the second frequency component.

2. The method of claim 1, further comprising determining, by the processing circuitry, a first characteristic of the first frequency component and a second characteristic of the second frequency component, wherein providing the indication of the location of the electrode in the patient comprises providing the indication of the location of the electrode in the patient based on the first characteristic and the second characteristic.

3. The method of claim 2, further comprising determining, by the processing circuitry, a relationship between the first characteristic and the second characteristic, wherein providing the indication of the location of the electrode in the patient comprises providing the indication of the location of the electrode in the patient based on the relationship between the first characteristic and the second characteristic.

4. The method of claim 3, wherein the relationship comprises a ratio of the first characteristic to the second characteristic.

5. The method of claim 2, wherein the first frequency component corresponds to a cardiac contraction frequency, the first characteristic comprises an amplitude of the first frequency component, the second frequency component corresponds to a respiration frequency, and the second characteristic comprises an amplitude of the second frequency component.

6. The method of claim 2, wherein the first characteristic and the second characteristic comprise one of an amplitude, frequency, wavelength, a power in Fourier space, or an intensity in the Fourier space.

7. The method of claim 1, wherein the first frequency component corresponds to a cardiac contraction frequency and the second frequency component corresponds to a respiration frequency, and wherein providing the indication of the location of the electrode in the patient comprises providing the indication of the location of the electrode relative to at least one of a heart or lungs of the patient.

8. The method of claim 1, wherein providing the indication of the location of the electrode comprises providing an indication of the location of the electrode relative to at least one of: a sternum; a heart; a lung; or a portion of the heart or the lung.

9. The method of claim 1, wherein providing the indication of the location of the electrode in the patient includes providing an indication of at least one of: a relative cranial-caudal location of the electrode, a relative left-right lateral location of the electrode, or a relative ventral-dorsal location of the electrode.

10. The method of claim 1, further comprising generating the impedance signal, identifying the first and second frequency components, and providing the indication of the location periodically over time as the location changes.

11. The method of claim 1, further comprising:
   generating, by the impedance measurement circuitry, a plurality of impedance signals, each of the impedance signals indicating impedance proximate to a respective one of a plurality of electrodes, the plurality electrodes coupled to the impedance measurement circuitry and including the electrode;
   identifying, by the processing circuitry and for each of the plurality of impedance signals, the first and second frequency components; and
   providing, by the processing circuitry and for at least one of the electrodes, an indication of the location of the electrode in the patient based on the first and second frequency components of the respective impedance signal.

12. The method of claim 11, wherein providing the indication of the location of the at least one of the plurality of electrodes in the patient comprises providing the indication of the location of the at least one of the plurality of electrodes based on the location of at least one other electrode of the plurality of electrodes.

13. The method of claim 11, wherein providing the indication of the location of the at least one of the plurality of electrodes in the patient comprises providing the indication of the location of the at least one of the plurality of electrodes based on the location of at least one other electrode of the plurality of electrodes based on a comparison of the first and second frequency components for the plurality of impedance signals.

14. The method of claim 1, wherein a range of frequency values of the first frequency component includes values of about 0.15 hertz to about 0.45 hertz, and a range of frequency values of the second frequency component includes values of about 0.66 hertz to about 1.66 hertz.

15. The method of claim 1, wherein providing the indication of the location of the electrode in the patient includes determining the location of the electrode without fluoroscopic imaging information.

16. The method of claim 1, wherein the electrode is positioned on a medical lead configured for implantation within a substernal space of the patient.

17. The method of claim 1, wherein the electrode is positioned on an implant tool configured for advancement into a substernal space of the patient, the implant tool defining a channel configured to receive a medical lead for implanting the medical lead in the substernal space.

18. The method of claim 1, further comprising determining, by the processing circuitry, that a measurement of the impedance signal satisfies a criterion.

19. The method of claim 18, further comprising providing, by the processing circuitry and to the user, a warning indication in response to determining that the measurement satisfies the criterion.

20. A medical device system comprising:
an electrode;
impedance measurement circuitry coupled to the electrode, the impedance measurement circuitry configured to generate an impedance signal indicating impedance proximate to the electrode; and
processing circuitry configured to:
identify a first frequency component and a second frequency component of the impedance signal; and
provide an indication of a location of the electrode in a patient based on the first frequency component and the second frequency component.

21. The medical device system of claim 20, further comprising a substernally implantable medical lead, the electrode disposed on the substernally implantable medical lead.

22. The medical device system of claim 20, wherein the processing circuitry is configured to determine a first characteristic of the first frequency component and a second characteristic of the second frequency component, wherein the processing circuitry is configured to provide the indication of the location of the electrode in the patient based on the first characteristic and the second characteristic.

23. The medical device system of claim 22, wherein the processing circuitry is configured to determine a relationship between the first characteristic and the second characteristic, wherein the processing circuitry is configured to provide the indication of the location of the electrode in the patient based on the relationship between the first characteristic and the second characteristic.

24. The medical device system of claim 22, wherein the first frequency component corresponds to a cardiac contraction frequency, the first characteristic comprises an amplitude of the first frequency component, the second frequency component corresponds to a respiration frequency, and the second characteristic comprises an amplitude of the second frequency component, and
wherein the processing circuitry is configured to determine the amplitude of the first frequency component and the amplitude of the second frequency component.

25. The medical device system of claim 22, wherein the first characteristic and the second characteristic comprise one of an amplitude, frequency, wavelength, or an intensity in the Fourier space.

26. The medical device system of claim 23, wherein the relationship comprises a ratio of the first characteristic to the second characteristic, and wherein the processing circuitry is configured to determine the ratio.

27. The medical device system of claim 20, wherein the first frequency component corresponds to a cardiac contraction frequency and the second frequency component corresponds to a respiration frequency, and wherein the processing circuitry is configured to provide the indication of the location of the electrode in the patient relative to at least one of a heart or lungs of the patient.

28. The medical device system of claim 20, wherein the processing circuitry is configured to provide the indication of the location of the electrode relative to at least one of: a sternum; a heart; a lung; or a portion of the heart or the lung.

29. The medical device system of claim 20, wherein the processing circuitry is configured to provide an indication of at least one of: a relative cranial-caudal location of the electrode, a relative left-right lateral location of the electrode, or a relative ventral-dorsal location of the electrode.

30. The medical device system of claim 20, wherein the impedance measurement circuitry is configured to generate the impedance signal, wherein the processing circuitry is configured to identify the first and second frequency components, and wherein the processing circuitry is configured to provide the indication of the location periodically over time as the location changes.

31. The medical device system of claim 20, wherein the processing circuitry is configured to provide the indication of the location of the electrode in the patient without fluoroscopic imaging information.

32. The medical device system of claim 20, wherein the electrode is positioned on an implant tool configured for advancement into a substernal space of the patient, the implant tool defining a channel configured to receive a medical lead for implanting the medical lead in the substernal space.

33. The medical device system of claim 20, further comprising a lead, wherein the electrode is disposed on the lead, and wherein a proximal end of the lead includes a connector to connect the lead to a medical device.

34. The medical device system of claim 33, further comprising a plurality of electrodes disposed on the lead, wherein the impedance measurement circuitry is configured to generate a plurality of impedance signals, each of the impedance signals indicating impedance proximate to a respective one of the plurality of electrodes, the plurality electrodes coupled to the impedance measurement circuitry and including the electrode.

35. The medical device system of claim 34, wherein the processing circuitry is configured to identify for each of the plurality of impedance signals, the first and second frequency components, and wherein the processing circuitry is configured to provide for at least one of the electrodes, an indication of the relative location of the electrode in the patient based on the first and second frequency components of the respective impedance signal.

36. The medical device system of claim 20, wherein the processing circuitry is configured to determine that a measurement of the impedance signal satisfies a criterion.

37. The medical device system of claim 36, wherein the processing circuitry is configured to provide a warning indication to the user in response to determining that the measurement satisfies the criterion.

38. A medical device system comprising:
an electrode;

impedance measurement circuitry coupled to the electrode, the impedance measurement circuitry configured to generate an impedance signal indicating impedance proximate to the electrode; and processing circuitry configured to:
- identify a first frequency component of the impedance signal corresponding to a cardiac contraction frequency and a second frequency component of the impedance signal corresponding to a respiration frequency;
- determine a first amplitude of the first frequency component and a second amplitude of the second frequency component;
- determine a relationship between the first amplitude and the second amplitude; and
- provide an indication of a location of the electrode in a patient based on the relationship.

39. The medical device system of claim 38, wherein the relationship comprises a ratio of the second amplitude to the first amplitude.

40. The medical device system of claim 38, further comprising a user interface configured to provide an indication that the electrode is closer to a lung of the patient than a heart of the patient when the ratio is relatively larger, and configured to provide an indication that the electrode is closer to a heart of the patient than the lung of the patient when the ratio is relatively smaller.

\* \* \* \* \*